United States Patent
Schmoll et al.

(10) Patent No.: US 10,092,364 B2
(45) Date of Patent: Oct. 9, 2018

(54) FLOW CONTROL IN COMPUTER-ASSISTED SURGERY BASED ON MARKER POSITION

(75) Inventors: Rainer Schmoll, Munich (DE); Sven Flossman, Feldkirchen (DE); Alexander Schaal, Dachau (DE); Axel Besinger, Bad Zwischenahn (DE); Johannes Manus, Munich (DE)

(73) Assignee: Brainlab AG, Munich (DE)

( * ) Notice: Subject to any disclaimer, the term of this patent is extended or adjusted under 35 U.S.C. 154(b) by 825 days.

(21) Appl. No.: 13/635,027

(22) PCT Filed: Mar. 17, 2010

(86) PCT No.: PCT/EP2010/053440
§ 371 (c)(1),
(2), (4) Date: Sep. 14, 2012

(87) PCT Pub. No.: WO2011/113483
PCT Pub. Date: Sep. 22, 2011

(65) Prior Publication Data
US 2013/0006270 A1 Jan. 3, 2013

(51) Int. Cl.
*A61B 19/00* (2006.01)
*A61B 34/20* (2016.01)
(Continued)

(52) U.S. Cl.
CPC .............. *A61B 34/20* (2016.02); *A61B 34/10* (2016.02); *A61B 34/25* (2016.02);
(Continued)

(58) Field of Classification Search
USPC ............... 600/407, 425, 426, 429, 340, 443; 606/130
See application file for complete search history.

(56) References Cited

U.S. PATENT DOCUMENTS 6,322,567 B1 * 11/2001 Mittelstadt et al. .......... 606/130
8,719,327 B2 * 5/2014 Blevins .................. G05B 11/42
702/185
(Continued)

FOREIGN PATENT DOCUMENTS

DE           196 39 615           4/1998
DE     10 2004 049 258 A1        4/2006
(Continued)

OTHER PUBLICATIONS

International Search Report and Written Opinion for International Application No. PCT/EP2010/053440 dated Dec. 2, 2010.
(Continued)

*Primary Examiner* — Jason Lin
(74) *Attorney, Agent, or Firm* — Tucker Ellis LLP

(57) ABSTRACT

The invention is in particular directed to a data processing method for use in computer-assisted surgery, comprising the following steps: a) providing marker data which describe a spatial arrangement of at least one marker device and/or a change in a relative spatial arrangement of at least two marker devices (5, 6, 7); b) providing condition data which describe a condition for the spatial arrangement of at least one marker device and/or a condition for the change in the relative spatial arrangement of the at least two marker devices (5, 6, 7); and c) controlling a control flow of the data processing method on the basis of the marker data and the condition data.

18 Claims, 5 Drawing Sheets

(51) Int. Cl.
*A61B 34/00* (2016.01)
*A61B 34/10* (2016.01)
*A61B 90/00* (2016.01)

(52) U.S. Cl.
CPC ............... *A61B 2034/2055* (2016.02); *A61B 2034/2068* (2016.02); *A61B 2034/254* (2016.02); *A61B 2034/256* (2016.02); *A61B 2090/368* (2016.02)

(56) References Cited

U.S. PATENT DOCUMENTS

| | | | | |
|---|---|---|---|---|
| 9,076,212 | B2* | 7/2015 | Ernst ..................... | A61B 5/055 |
| 2003/0153829 | A1* | 8/2003 | Sarin ..................... | A61B 5/103 |
| | | | | 600/426 |
| 2004/0106916 | A1* | 6/2004 | Quaid .................... | A61B 34/71 |
| | | | | 606/1 |
| 2005/0203384 | A1* | 9/2005 | Sati ....................... | A61B 6/547 |
| | | | | 600/426 |
| 2005/0253870 | A1* | 11/2005 | Kotake et al. ......... | 345/633 |
| 2006/0171560 | A1* | 8/2006 | Manus .................. | H04N 7/181 |
| | | | | 382/103 |
| 2007/0049819 | A1 | 3/2007 | Stifter et al. | |
| 2007/0073137 | A1* | 3/2007 | Schoenefeld .......... | A61B 90/36 |
| | | | | 600/407 |
| 2007/0129626 | A1* | 6/2007 | Mahesh ................. | G16H 40/63 |
| | | | | 600/407 |
| 2007/0232900 | A1* | 10/2007 | Hoheisel ............... | A61B 90/36 |
| | | | | 600/424 |
| 2008/0047170 | A1* | 2/2008 | Nichols ................. | E02F 3/435 |
| | | | | 37/348 |
| 2008/0077158 | A1 | 3/2008 | Haider et al. | |
| 2008/0119725 | A1* | 5/2008 | Lloyd .................... | A61B 90/36 |
| | | | | 600/424 |
| 2008/0154125 | A1* | 6/2008 | Maier .................... | A61B 90/36 |
| | | | | 600/424 |
| 2008/0287803 | A1* | 11/2008 | Li .......................... | A61B 5/06 |
| | | | | 600/466 |
| 2008/0309632 | A1 | 12/2008 | Westerman et al. | |
| 2009/0281419 | A1* | 11/2009 | Troesken ............... | A61B 5/06 |
| | | | | 600/424 |
| 2010/0168763 | A1* | 7/2010 | Zhao ..................... | A61B 34/30 |
| | | | | 606/130 |
| 2010/0185087 | A1* | 7/2010 | Nields ................... | A61B 18/18 |
| | | | | 600/439 |

FOREIGN PATENT DOCUMENTS

| | | |
|---|---|---|
| DE | 10 2006 015 349 A1 | 10/2007 |
| DE | 10 2007 057 094 A1 | 5/2008 |
| EP | 1 510 181 | 3/2005 |
| EP | 1 579 803 A1 | 9/2005 |
| EP | 1 615 109 | 1/2006 |
| EP | 1 791 070 A2 | 5/2007 |
| EP | 2 547 278 B1 | 10/2016 |
| WO | 2004001569 A2 | 12/2003 |

OTHER PUBLICATIONS

European Office Action for European Patent Application No. 10 710 564.5 dated Jan. 30, 2015 (4 pages).
European Patent Office, Communication of opposition, corresponding to EP application No. EP2547278, dated Jul. 13, 2017, 6 pages.
Merkmalsanalyse des unabhangigen Anspruches 1 des Streitpatents EP 2 547 278, A 178 007 3., Jul. 5, 2007, e-364, 1 page.

\* cited by examiner

|   | A | B | C | D | E | F |
|---|---|---|---|---|---|---|
| 1 |   |   |   |   |   |   |
| 2 | m1 |   | m4 |   | ↑<br>m3 |   |
| 3 |   |   |   | m4' |   |   |
| 4 |   |   | m2<br>↓ |   |   |   |
| 5 |   |   |   | ↻<br>m5 |   |   |
| 6 |   |   |   |   |   |   |

Figure 3

FLOW CONTROL IN COMPUTER-ASSISTED SURGERY BASED ON MARKER POSITION

This application is a national phase of International Application No. PCT/EP2010/053440 filed Mar. 17, 2010 and published in the English language.

The present invention is directed to a data processing method for use in computer-assisted surgery, in particular image-guided surgery, more specifically for controlling (in particular changing) the control flow of the data processing method, in particular a navigation method. As part of the invention, a program and a navigation system which is configured to execute the data processing method in accordance with the invention are also disclosed. The expression "controlling the control flow" is also abbreviated here to "flow control".

Flow control in image-guided surgery and/or surgical navigation methods is currently performed using a touch screen which is typically operated by the surgeon or the surgeon's assistants. The touch screen is normally provided with a panel comprising workflow control fields. These can for example be used to enter or activate a part of the navigation method, for example to zoom-in the visual display to an anatomical region which is of interest to the surgeon. A number of problems arise within this context. Firstly, the touch screen panel may not be sterilised; secondly, the surgeon's attention is turned away from the patient and/or the operation field when using the touch screen.

EP 1 510 181 discloses detecting a rotation of a pointer instrument around its longitudinal axis in order to interactively control a navigation station. Reference is also made to DE 196 39 615, EP 1 615 109 and US 2008/309632.

One problem to be solved by the invention is to make flow control in image-guided surgery more reliable and in particular less distracting for the user.

This problem is solved by the subject-matter of the independent claims, wherein the dependent claims disclose preferred embodiments of the invention. Features from different embodiments can be combined with each other.

The method according to the invention can be used in image-guided surgery, in particular computer-assisted surgery and/or surgical navigation. The method can be implemented by a navigation system for use in computer-assisted surgery, in particular image-guided surgery.

The method in accordance with the invention is preferably embodied by a data processing method, more preferably a data processing method for use in computer-assisted surgery, in particular a navigation method.

The method in accordance with the invention can even more preferably also be embodied by a method for processing technical data, more specifically a method for controlling a navigation system.

Marker data are provided in accordance with the method of the invention. The marker data describe the spatial arrangement of at least one marker device and/or a change in the relative spatial arrangement of at least two marker devices (for instance, in a reference system). In particular, the marker data describe the spatial arrangement of at least one marker device in a reference system of the data processing method, which is for instance the reference system of the navigation system. In particular, the marker data describe the relative spatial arrangement of at least two marker devices. The marker data can be time-dependent and describe a current status of the relative spatial arrangement and/or change in the relative spatial arrangement of the at least two marker devices. The marker data can be generated by detecting the marker devices, as explained below. The spatial arrangement of at least one marker device is in particular described by the position of the marker device (in particular in the reference system). Alternatively or additionally, the spatial arrangement of the at least one marker device can be described by the presence or absence of the at least one marker device in a region (see "region state" below). A variety of regions can be defined within the reference system. In particular, it is possible to determine the absence or presence of a marker device in any of these regions on the basis of the position of the marker device (as described by the marker data).

In accordance with method of the invention, condition data are preferably provided. The condition data comprise conditions for a spatial arrangement of at least one marker device and/or a change in a relative spatial arrangement of at least two marker devices. In particular, the condition data comprise a condition for the relative spatial arrangement of at least two marker devices. An example of this condition for a spatial arrangement of a marker is in particular a condition for a position of the marker device. In particular, a condition for a so-called region state is the presence or absence of a marker device (in particular a single marker) in a particular region and/or the presence or absence of a plurality of marker devices (in particular single markers) in a plurality of regions according to a predefined pattern. Said region or regions is/are in particular defined in a reference system, as mentioned above. Thus, according to one step of the method in accordance with the invention, condition data which in particular represent a condition for a relative spatial arrangement of a set of marker devices, in particular at least two marker devices (for example, a first marker device and a second marker device) are provided. Alternatively or additionally, the condition data represent a condition for a change in the relative spatial arrangement of the at least two marker devices. Within the context of this invention, a condition "for" something preferably means a condition which is to be met by something. If, for example, a condition is said to be "for" certain data or a certain physical variable, the method in accordance with the invention preferably comprises a step of evaluating the respective data of said physical variable with regard to whether they fulfil the aforesaid condition. The condition or conditions for a relative spatial arrangement of the marker devices and/or changes in it is/are preferably described by pattern data. The pattern data represent a pattern which can be derived from the positions (in particular, relative positions) of the marker devices.

As mentioned above, marker data and condition data are preferably provided in accordance with the invention. The control flow of the data processing method is preferably controlled on the basis of these data. This control is preferably based on a comparison of the marker data and the condition data. In particular, the marker data are checked to see if they describe a relative spatial arrangement and/or change in the relative spatial arrangement of the marker devices which fulfils the condition described by the condition data. This check is preferably made by comparing the marker data and the condition data. A determination is made on the basis of the comparison as to whether or not the condition described by the condition data is met by the relative spatial arrangement and/or the change in the relative spatial arrangement of the at least two marker devices, as described by the marker data. If the condition is met, the control flow is controlled, in particular changed, in particular using a control flow statement which is predefined for the scenario in which the condition is fulfilled.

The control flow of the data processing method is in particular controlled as described above by means of a control flow statement. This control flow statement can for example have any of the following different effects: continuing the control flow at a different statement; executing a set of statements only if a certain condition is met; executing a set of statements zero or more times until a condition is met; executing a set of remote statements, after which the control flow usually returns; and stopping the program, in particular preventing any further execution.

A (stored) assignment (link) between the condition data and the type of change in the control flow (in particular, a control flow statement) is preferably provided. Preferably, different conditions of a plurality of conditions are respectively assigned to different control flow statements of a plurality of control flow statements. The assignment can for example be injective or bijective, i.e. particular conditions are preferably linked to particular control flow statements. Thus, the control flow statement is executed if the assigned condition is fulfilled. A control flow statement is in particular selected from a plurality of control flow statements depending on the fulfilled condition and based on the assignment. The assignment can be implemented by a look-up table. Thus, the step of "controlling the control flow" in particular comprises the step of determining a control flow statement (in particular, selecting a control flow statement from a plurality of control flow statements). An additional link to the control flow history is preferably also provided, i.e. only if there has been a particular control flow history, in particular only if one or more predetermined control flow statements have been previously executed, is a particular control flow statement executed (providing any other conditions defined by the condition data are also fulfilled). As will be discussed below, the condition described by the condition data can relate to the current situation described by the marker data and/or can also relate to a previous situation, as also described by the marker data and/or by a control flow statement or a plurality (in particular, a sequence) of control flow statements which is/are to have been previously executed. Thus, for instance, only if a particular trajectory of marker devices and/or a particular sequence of control flow statements has previously existed, is a particular predefined control flow statement. Preferably, the link between the condition and a particular control flow statement which is executed if the condition is fulfilled is stored in a database, in particular a database of the navigation system. The link can in particular be stored in the form of a look-up table. In accordance with another embodiment, the condition for the control flow history is included in the condition data.

The condition for a change in the relative spatial arrangement is preferably such that it can only be met by a movement which includes a movement of all the extreme parts of at least one of the at least two marker devices. In particular, the condition is specified by defining such a movement, in particular the movement of the extreme parts. In particular, the condition is such that it can only be met by a movement which includes a translational relative movement of the at least two marker devices or by a translational movement of at least one of the at least two marker devices. In particular, the condition is specified by defining such a movement, in particular the translational movement. A translational movement of a marker device in particular includes a movement of all the parts (points) of a marker device. In particular, all the lines joining the initial and final parts (points) of the marker device are a set of parallel lines. The conditions disclosed herein and for example mentioned above preferably describe conditions for the spatial arrangement of the marker devices which can be unambiguously detected by any marker detection devices. In particular, the spatial arrangement can reflect the present situation in an operating theatre. This situation can in particular be unambiguously reflected by distances and/or changes in distance between the marker devices and/or by the presence or absence of a marker device. Thus, in accordance with the present invention, it is possible to control the flow control in accordance with conditions which reflect situations or a history of situations. The invention thus enables an intelligent situation-dependent flow control which makes flow control more reliable and less distracting. If the conditions imply or include a movement along a path or a distance between two subsequent positions of a marker device, then the path length or distance is in particular longer than a minimum length such as for example 0.5 cm, 1 cm, 2 cm, 5 cm or 10 cm. In particular, the condition defines such a minimum length. The conditions are in particular such that the path of movement of all the extreme parts of a marker device and/or the path of the translational movement of a marker device have a length which is longer than a minimum length such as for example 0.5 cm, 1 cm, 2 cm, 5 cm or 10 cm. This can advantageously increase the extent to which the conditions can be unambiguously detected.

The marker devices can in particular be displaced with respect to each other. In particular their relative spatial arrangement, in particular their relative position, can change. The condition data preferably describe a condition for such a change, while the change is preferably described by the marker data. The marker devices are in particular not (mechanically) fixed to each other. Their spatial relationship is in particular not predetermined and is not fixed. The relative spatial arrangement of the marker devices in particular denotes a spatial relationship of the marker devices relative to one another. The relative spatial arrangement thus comprises the position of the marker devices relative to one another (their relative position) and advantageously also their orientation relative to one another (their relative orientation). The relative position is advantageously characterised by the distance between the marker devices and preferably also by directional information, in particular a vectorial representation of the distance. Preferably, the relative orientation is described in particular by the positions of at least two points of one marker device relative to the positions of at least two points on another marker device (the relative position of each point being described with regard to at least one other point) and advantageously by a certain directional relationship of the vectors describing the relative positions of the points. The spatial positions (and in particular orientations) of the marker devices can in particular be individually detected and identified as being different (by a navigation system). In particular, the condition data include pattern data which comprise information describing a relative spatial arrangement and/or a change in the relative spatial arrangement of the at least two marker devices, i.e. a change in the position (in particular the distance and/or orientation) of the at least two marker devices relative to one another. The marker device is in particular an (asymmetrical) rigid body. The change in position of the marker devices can in particular be specified (or needs to be specified) by six degrees of freedom. Where "at least one marker device" is mentioned here, this is of course also intended to encompass the meaning of "at least two marker devices". Where "at least two marker devices" is mentioned here, this is of course also intended to encompass the meaning of "at least three marker devices".

Where data are "provided", this means that they are ready for use by the method in accordance with the invention. The data can for instance achieve this state of being "provided" by being inputted (for example via interfaces). The data can also achieve this state by being stored in a memory (for example a ROM, CD and/or hard disc) and thus ready for use within the framework of the method in accordance with the invention. The data are preferably generated before being provided, for instance by being detected or captured (for example by an analysis apparatus and/or a camera system), or the data can be provided by being determined in a previous step.

It is the function of a marker device to be detected by a marker detection device (for example, a camera or an ultrasound receiver), such that its spatial arrangement (i.e. its spatial position and/or orientation) can be ascertained and corresponding marker data generated. In particular, the marker data are generated based on the detection, in particular generated from electric signals generated due to the detection of marker devices. The detection device is in particular part of a navigation system. A marker device comprises or consists of at least one marker. The marker devices can comprise or consist of active markers. An active marker can for example emit electromagnetic radiation and/or waves, wherein said radiation can be in the infrared, visible and/or ultraviolet spectral range. The marker device can also however comprise or consist of passive markers which can for example reflect electromagnetic radiation in the infrared, visible and/or ultraviolet spectral range. To this end, the markers can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or a set of one or more (individual) markers in a predetermined spatial relationship. A marker device comprises one, two, three or more markers (in particular, a plurality of markers) in a predetermined spatial relationship. This predetermined spatial relationship is in particular known to a navigation system and for example stored in a computer of the navigation system.

The relative positions of a first marker device relative to a second marker device are preferably described by the marker data and can change. This change is also preferably described by the marker data. The marker devices can in particular be fixed to different physical structures (such as instruments or implants or parts of a body) which can be individually moved. This can result in a change in position. The aforementioned conditions in particular specify such changes.

In accordance with the invention, a change in the relative spatial arrangement can in particular be due to a movement of extreme parts of at least one of the at least two marker devices. The aforementioned conditions in particular specify such a change. Such a movement preferably involves all the extreme parts of said marker device. The conditions in particular specify such a movement. The movement of the extreme parts is in particular a movement of a marker device relative to another marker device. The conditions in particular specify such a movement. An extreme part of a marker device is in particular understood to be a part of the marker device which is not located at or near the centre—in particular the centre of gravity and/or the geometric centre—of the marker device. The extreme parts for example comprise end parts and/or outer (i.e. peripheral) parts of the marker device. In accordance with the invention, the conditions for a movement of the respective marker device (i.e. the change in relative spatial arrangement between the marker devices) comprises for example a condition for a translational movement of the at least one of the at least two marker devices relative to another of the at least two marker devices. However, a rotating movement (i.e. a rotation) of a marker device, in particular around a rotational axis which is outside of a longitudinal extension of the marker device (and advantageously intersects the longitudinal extension, preferably at an angle of 90 degrees, and is preferably not parallel to the longitudinal extension) is also an example of a condition for the movement (of all the extreme parts). A translational movement in particular denotes a movement of a marker device during which all the points (i.e. parts) of the marker device are moved in the same direction, i.e. in parallel directions.

If the moving marker device is a reference star, the extreme parts of the marker device can for example be the end of the holding element which is distal with regard to the position of the marker and/or markers attached to the reference star, and/or the extreme parts can be the markers themselves. If the marker device is a pointer, the extreme parts of the pointer can for example be the end of the handle which, when the pointer is used, is positioned proximally with regard to a user. Alternatively or additionally, the distal end of the pointer, i.e. the end pointing away from the user and preferably towards a location to be identified by the pointer, can be an extreme part.

A "reference star" is an example of a marker device and refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable the corresponding reference star to be identified by a navigation system on the basis of the position of the markers relative to each other. It is therefore also then possible for the objects (for example, instruments and/or parts of a body) to which the reference star is attached to be identified and/or differentiated. In a surgical navigation method, the reference star serves to attach a plurality of markers to an object (for example, a bone or a medical instrument) in order to be able to detect the arrangement of the object (i.e. its spatial position and/or orientation). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

The marker devices used for generating the marker data which are processed by the method are in particular not identical to one another and can be of different types. In particular, the first marker device can for example comprise a passive marker and the second marker device can for example comprise an active marker. The marker devices can however also be of the same type but exhibit different relative spatial relationships between the markers, such that the marker devices can be distinguished from one another (in particular due to a different geometric arrangement of the markers). The marker data preferably include information which allows the identity of the marker device, and in particular the object to which the marker device is attached, to be determined. Said information preferably comprises information on the relative positions of the markers of a marker device and in particular an allocation (for example in the form of a look-up table) between these positions and an identity (marker identity).

The positions of the two marker devices are preferably determined in a reference system (co-ordinate system) which is common to both markers (i.e. the positions of both markers are determined within the same reference system). The reference system can for example be centred on one of the markers or another entity which is used for performing the method (such as for example the detection device) or any other arbitrary point. This reference system is preferably the same one as that used by the navigation system. The positions can be described in preferably three-dimensional co-ordinates such as Cartesian co-ordinates or spherical co-ordinates. In the specific case of spherical co-ordinates, polar co-ordinates can be used.

The marker data preferably comprise position data which include information on the position of the marker devices, such as information about the presence or absence of marker devices, in particular in a region such as the detection field and/or the field of view of the detection device. Examples scenarios are: a first marker device is present and a second marker device is absent; both marker devices are absent; both marker devices are present. This information about the (in particular simultaneous) presence or absence of a number of marker devices (preferably one or two or more marker devices), in particular in each of a number of regions (for example, one or two or more regions), in particular for each of a number of lengths of time (for example, one or two or more lengths of time), represents an example of a pattern which is derived from positions of the marker devices. A length of time of the presence or absence of a marker device in a region, which is necessary for a condition to be fulfilled, is defined by the pattern, in particular for each region, respectively. The pattern derived from positions of the marker devices is also referred to as "pattern information" or "pattern" for short. The condition data in particular describe such a pattern. Such a pattern can thus represent a condition. If this condition is met by the pattern described by the marker data, then instructions are executed which in turn control the control flow. The pattern described by the condition data can therefore also be referred to as an "instruction pattern" and can be used to change a control flow which is used during computer-assisted surgery, in particular if the marker data fulfil the instruction pattern and optionally also if the control flow meets a particular condition, i.e. if the status of the control flow meets a particular condition, for instance whether a particular step (in particular, a statement) of the control flow has been reached and/or has previously been reached and/or has not yet been reached. The condition represented by the condition data therefore preferably defines an instruction pattern. The condition data in particular contain information on a pattern which, when reflected by the marker data and judged to fulfil the condition defined by the condition data, results in an instruction for controlling the control flow. In particular, a change in the control flow results, in that a subsequent step is executed which is different to the next step in the normal control flow (without changes).

The conditions for the relative spatial arrangement of the marker devices can be defined not only by the presence of certain marker devices, in particular in a predefined region, but also by the absence of certain marker devices (in this context, the plural form "marker devices" is intended to encompass the singular), in particular in a predetermined region. The conditions can in particular involve positions of marker devices relative to one another or relative to one or more other entities (which are preferably not marker devices), in particular their distance from one or more other marker devices and/or entities. A control flow of the data processing method is in particular controlled by changing the control flow in accordance with the pattern of positions of marker devices, preferably in accordance with a difference between positions, in particular a difference determined on the basis of the marker data which describe the previous position and the present position of a marker device. The conditions described by the condition data can be described not only by conditions for the relative spatial arrangement and/or conditions for the spatial change in the relative spatial arrangement (such as an upward/downward movement, the magnitude of velocity, etc.) but also or alternatively by conditions for the change in the relative spatial arrangement over time. The first two conditions are also referred to here as spatial conditions, while the latter is also referred to as a temporal condition. The spatial conditions are in particular derived from the positions of the at least two marker devices. The positions are in particular defined in a reference system used by the data processing method.

A condition for the relative spatial arrangement and/or the change in the relative spatial arrangement is in particular dependent on time. This means that a condition preferably has to be fulfilled within or for a certain length of time (time interval) and/or at a certain point in time and/or between certain points in time. Whether this condition is met is decided on the basis of the marker data, in particular by analysing the marker data. Preferably, the length of time (i.e. time interval) for a time-dependent condition can be set to any length of time between a few seconds (for example, five seconds or ten seconds) and one or more minutes. In particular, all the parts of a pattern to which the condition is applied should be realised within the time interval. This helps to avoid marker device movements (as described by the marker data) being incorrectly identified as an instruction pattern, for example by randomly performing movements with marker devices over an arbitrary time interval without considering that an instruction pattern may be fulfilled. Thus, the marker data are preferably analysed on the basis of this time-dependent condition, in order to determine whether the condition described by the condition data is fulfilled.

One example of pattern information is information on a change in position (as an example of a change in the relative spatial arrangement), in particular information on the motion state of the marker devices. One example of a pattern of motion states (a motion state pattern) would be if a first marker device is moving upwards, a second marker device is moving downwards and another marker device is at rest. If this motion state pattern is fulfilled, then the control flow is changed. This motion state pattern thus represents an example of an instruction pattern. The information on the motion state is advantageously included in the marker data. The information on the motion state of the marker devices in particular comprises information about the modulus (i.e. magnitude) and/or direction of the velocity of the marker devices and can preferably be determined by calculating a temporal derivative, in particular a temporal derivative of a temporal series of the detected positions (in particular a pattern, preferably a temporal and spatial pattern, of the detected positions). The direction of velocity in particular comprises the direction of a translational movement. The condition data in particular describe a condition for the length of time to have elapsed since it has been determined that the marker data fulfil the spatial conditions. The condition data can in particular describe a temporal series of positions. Such a temporal series preferably represents a temporal and spatial pattern of marker positions. In particular, if the condition for a motion state describes a condition for a velocity or an acceleration in a movement, then this preferably includes a condition for a velocity or acceleration in a translational movement or a movement in which all the extreme parts are moved.

The term "motion state" also includes the possibility of the marker devices being at rest (in particular, within their reference system), in particular for a predetermined length of time, i.e. of having a static status with a velocity vector equal to a zero vector. The state of marker devices being "at rest" preferably denotes a state of the marker devices in which they are not moving within their reference system. Alternatively or additionally, it can denote that the marker devices are at rest relative to each other within their reference system, i.e. that they are not moving relative to one another. In this case, the condition data in particular comprise a temporal condition which for example describes how long the marker device is at rest and/or for instance a sequence (history) of spatial conditions. This sequence can be a discrete sequence, such as the absence and then presence of a marker device in a particular region, or a continuous sequence, such as the zigzag movement discussed below.

Depending on which meaning is used, the velocity and/or the velocity vector can describe the movement of the marker devices with respect to their reference system or relative to one another (the latter case can be referred to as the "relative velocity"), in particular a change in the spatial arrangement of the marker devices. The acceleration and/or acceleration vector can be used analogously.

As mentioned above, the motion states can be used to describe the instruction pattern; specifically, the position of at least one of the marker devices can be used as a condition, and the motion state of at least another of the marker devices can be used as a condition, in order to determine how to control the control flow of the method. Information about the motion state of more than one of the marker devices can also be used to this end.

The marker data and/or the condition data preferably comprise information about the position of at least two markers (i.e. position data) and/or information about the motion state of at least one marker (i.e. motion state data). In particular, marker data describing a relative movement between two marker devices and/or a continuous trajectory and/or a (discrete) sequence of positions of marker devices trigger an instruction to the surgical navigation system to control the control flow of the data processing method, in particular the control flow of the navigation procedure. The trajectory or sequence of positions is in particular realised by a movement which includes translational movements of the marker devices.

Another example of pattern information would be if a first marker is in a particular motion state (for example, moving) while a second marker is within a particular region (in particular, a spatial region). This pattern refers both to motion states of a marker and to region states (in particular the presence in and/or absence from a region) of a marker. Such a pattern is also referred to as a motion-region pattern and is an example of an instruction pattern.

Corresponding information is advantageously included in the motion-region data which can be included in the condition data. Patterns which only describe region states (i.e. the presence and/or absence of marker devices in regions) are also referred to as "region patterns", wherein corresponding information is advantageously included in region data which can be included in the pattern data. Region patterns also represent an example of instruction patterns. Region patterns can include temporal conditions or can be combined with temporal conditions, i.e. the time, in particular the length of time of the presence and/or absence of at least one marker device is defined for at least one region, in order to define the condition (instruction pattern).

The marker positions can be determined in a reference system (a co-ordinate system) which uses rectangular and/or polar and/or spherical co-ordinates. As an example of rectangular co-ordinates, Cartesian co-ordinates in two or three dimensions can be used. Marker positions are preferably determined by dividing the area in which the positions are expected (also referred to here as the "operating area"), in particular a field of view of the detection device and/or the space used or envisaged for performing the method according to the invention, into predetermined geometric divisions which are examples of the above-mentioned regions. Advantageously, the marker data are used to determine whether or not a marker device is lying in one of these predetermined divisions. Depending on this, a decision is made as to whether the conditions for a change in the control flow are met, i.e. whether the instruction pattern is fulfilled. The operating area can for example be divided into two-dimensional zones comprising polygonal shapes or three-dimensional volumes comprising polyhedral shapes. A circular or at least partly circular shape of the zones or a spherical or at least partly spherical shape of the volumes can also be defined. The operating area is therefore preferably divided into delineated geometric divisions (regions) using a grid-based co-ordinate system (a grid) which comprises division boundaries and nodes at which the division boundaries intersect one another.

In accordance with the invention, it is also possible to define paths through such geometric divisions, for example by predefining a sequence of zones and/or volumes through which the marker device is to pass over time in order to create an instruction pattern. An instruction pattern can thus be defined by the presence of marker devices in specific geometric divisions in a predetermined sequence, in particular combined with a time interval within which such a sequence is to be performed. An instruction pattern can also be defined by two or more marker devices following a predetermined movement pattern relative to one another or having predetermined positions relative to one another. Using such a geometric division of the operating area has the specific advantage that a marker device which is used for determining an instruction pattern can for example be moved a minor distance without meeting the conditions described by the instruction pattern, for example as long as its position does not move out of a predetermined geometric division or a number of predetermined and preferably coherent and/or neighbouring geometric divisions. This for example enables a user to move a marker device out of the way, for example if the marker device is interfering with other devices used for performing computer-assisted surgery, without disrupting the control flow of the data processing method.

It is also possible to determine whether for example an entity to which the marker device (the position of which has been determined) is attached is currently located in a geometric division in which its presence is unfavourable. The geometric divisions can for example be used to define regions in which certain entities (such as for example an instrument table, X-ray machines, persons—in particular, a patient) should not be located while computer-assisted surgery is being performed. If the position of such an entity, to which the detected marker device is attached, is found to be in a region (prohibited region) in which its position preferably should not lie, then a corresponding warning signal can be issued to a user via the indication device of the navigation system being used to perform the method of the invention. The condition data then include a condition for the presence of said marker device in such a region. If the marker data indicate such a presence, the condition is met and the control flow is controlled so as to initiate a corresponding warning signal. To this end, and preferably as another condition, marker identity data (such as are described further below) can be used so that the warning signal is only issued if a particular object or type of object, to which the marker device is attached, is found to be situated in the prohibited region. Another example of a condition for a spatial arrangement of a marker device, in particular a single marker device, is that the marker device is situated in a particular position and/or a particular region for a certain length of time. If it is determined, on the basis of the marker data, that this condition is fulfilled, then the control flow of the data processing method is controlled, in particular changed. Thus, a spatial condition for a spatial arrangement of at least one marker device is preferably combined with a temporal condition which in particular specifies the time in which the spatial condition (the condition for the spatial arrangement of the at least one marker device) has to be fulfilled. The condition for the spatial arrangement of the at least one marker device is in particular such that it can be fulfilled if the marker data describe a static, i.e. non-moving, marker device. The condition can in particular be fulfilled if the static status of the marker device (as described by the marker data) is maintained for a length of time described by the temporal condition.

As mentioned above, regions can be determined by geometric spatial divisions. Regions can in particular be determined in accordance with the position of objects in the room. In accordance with another embodiment, the regions are determined on the basis of the positions of marker devices. In particular, the operating space is partitioned into regions and/or the geometry (size and/or shape) of the regions is determined on the basis of the geometry (size and/or shape) and/or the position of the marker devices. A marker device can for example comprise three markers (for example, three marker spheres) which lie in a common plane and thus define a plane. This plane then divides the operating space into two halves. Each half can represent one region. Three marker devices which are in particular not fixed to each other and which can in particular be moved relative to each other can likewise define a plane which divides the operating space into two regions. The partition of the operating space and therefore the regions can thus change dynamically if the marker devices are moved. If there are four individual marker devices, then each of the marker devices can define a corner of a region which has the shape of a pyramid. The markers themselves and/or the marker devices can thus define the size and shape of a region. Other examples will be given below. In accordance with this embodiment, the regions can in particular change dynamically; in particular, the geometry and/or position of the region can change due to a change in the position of (one or more) marker devices.

When a certain (i.e. predetermined) pattern is detected, this advantageously causes an instruction and/or command to be generated by and/or sent to the navigation system, as described below in more detail. Such a predetermined pattern is also referred to as an instruction pattern. An instruction pattern is preferably identified by comparing the detected pattern with the predetermined pattern, in particular by comparing the detected pattern information with predetermined pattern information.

Another step in the method in accordance with the invention is to control a control flow of the data processing method in accordance with the marker data and the condition data provided in a previous method step. A control flow of the data processing method is in particular understood to comprise a number of steps of the method (i.e. a sequence of method steps). The sequence of method steps can comprise all the steps of the data processing method or only a selection of steps. The control flow preferably also comprises branches and/or triggering predefined functions used in the method. The control flow can be embodied by a control program which is executed on a digital data processing device (for example, a computer). "Control flow" refers to the order in which the individual statements, instructions or function triggers of an imperative program or functional program (in particular, a program comprising the steps of the method in accordance with the present invention) are executed or evaluated.

Within an imperative programming language, a control flow statement is a statement which, when executed, results in a selection being made as to which of two or more paths is to be followed. An instruction pattern (in particular, information reflecting an instruction pattern) which has been determined from the marker data, as defined above, can be used as or translated into a control flow statement. A control flow statement is in particular executed in accordance with the marker data and the condition data. Therefore, controlling the control flow in particular comprises executing a control flow statement.

Within the context of this invention, controlling the control flow means for example triggering a procedure and/or file which can be executed or more generally a part of a program which is preferably used for performing the method in accordance with the invention. Controlling the control flow can also mean continuing to execute a procedure or part of a program which can be executed, if for example execution of the procedure or part of the program has been manually or automatically interrupted. The marker data which for example describe positions of the marker devices and/or the determined motions of the markers are preferably translated by the data processing method into a command to the data processing method, in particular to the surgical navigation system. They are preferably translated by means of the condition data.

Preferably, controlling the control flow of the method in particular comprises instructions to the data processing method, in particular to a navigation system, on modifying a visualisation view, for example a graphic output on a display device of the surgical navigation system. Modifying the visualisation view in particular comprises changing the perspective onto a part of a body which can in particular be represented by an image of the part of the patient's body which was taken before or during the operation and/or a graphic representation of a standard part of the body. The part of the body can for example be an anatomical structure such as a brain and/or a bone and/or a joint and can in general be any part of the body which is of interest to the user. Modifying the visualisation view can also involve changing the colour of different parts of the visualisation view and/or changing the magnification of the view, in particular a zoom ratio (this includes both a positive zoom ratio for increasing the magnification and a negative zoom ratio for decreasing the magnification). Controlling the control flow of the method can also comprise presenting a number of options for continuing the method, for a user to select, and/or asking the user to approve an instruction proposed by the data processing method, in particular by the navigation system.

In particular, controlling the control flow does not comprise any surgical activity in its narrower sense, such as using surgical instruments on a human or animal body in order for example to mechanically influence bones and/or tissue, i.e. the hard and/or soft constituents of the body. In particular, the control flow itself does not comprise any such activity. Other examples of steps in a control flow are: performing calculations on relative positions between marker devices; starting the motor of a drill; controlling the light intensity in the operating theatre; etc.

The modification made to the visualisation view, in particular the modified zoom value and/or zoom ratio, can preferably be locked. "Locking" the modified visualisation view means preventing the visualisation view from being modified further, even if an instruction pattern is detected which is equivalent to a command for a certain modification to be made to the visualisation view, in particular a change in the zoom factor. Thus, the visualisation view is not modified any further, despite a command situation having been detected. The lock can be activated automatically, for example by detecting a particular instruction pattern, and/or by user interaction such as for example a manual input at the surgical navigation system, in particular by activating a button on a touch screen. The lock can be released, such that further modifications to the visualisation view are (re-)enabled, for example in one of the ways described with respect to activating the lock.

The motion state (in particular the position) and/or the region state of at least one of the markers used in the method in accordance with the invention is preferably determined continuously, on the basis of the marker data which can change continuously. The continuous change in the marker data is in particular due to continuously detecting marker devices and thus continuously generating the marker data. The marker data are thus preferably generated on the basis of this continuous detection and (continuously) describe the motion state (in particular the position) and/or the region state as a function of time. Within this context, "continuous detection" includes detection at discrete time intervals (preferably at a detection frequency of a few Hertz, a few tens of Hertz or a few hundred Hertz and/or a detection frequency in a range having a lower limit of 1 Hz or 5 Hz or 10 Hz and/or an upper limit of 10 Hz or 50 Hz or 200 Hz or 1 KHz) over a continuous (in particular, uninterrupted) time interval—preferably, the duration needed to perform the envisaged procedures on the patient. Continuous detection, i.e. detecting at numerous discrete points in time separated by preferably constant intervals over a certain length of time, in particular leads to a history, in particular a temporal history of positions and/or motion states and/or region states. A temporal pattern of motion states (in particular positions) and/or region states can thus be determined from the marker data. A temporal pattern is thus preferably an example of an instruction pattern. Such a temporal pattern in particular contains information on a time-dependent pattern, in particular a sequence of patterns. The patterns in particular describe motion states and/or region states. Thus, an instruction pattern can be obtained on the basis of a temporal series of patterns which comprises information on motion states and/or region states, thus creating an instruction pattern which comprises or consists of a sequence of motion patterns and/or region patterns and/or motion-region patterns. This means that an instruction pattern does not have to be defined on the basis of an instantaneous measurement at a single point in time (a single measured value) alone, but can also be based on a temporal series of positions and/or motion states and/or region states of markers. This can enable the surgical navigation system to determine whether all the necessary steps of the predetermined user activity in the space detected by the navigation system (for example, the field of view of a stereotactic camera used as a detection device or, more generally, the operating area) have been performed before a predefined pattern described by the marker data is or in particular can be determined as an instruction pattern, i.e. identifying a situation described by the marker data as an instruction pattern can be path-dependent, in the sense that it depends on the positions and/or motion states and/or region states which have been previously passed through. This helps the user to avoid forgetting any steps in a predetermined user activity flow.

Controlling the control flow of the data processing method preferably results in a step of ascertaining a type of object, wherein the type is assigned to at least one of the marker devices. A marker device can be mechanically attached to a certain object (in particular, a medical object) such as a surgical instrument, a part of the patient's body and/or another object used during the operation such as an instrument table or a specific instrument or an implant. By using different marker properties (such as for example different reflective properties, emitting properties and/or geometric arrangements of markers on a reference star) for different objects as mentioned above (preferably, non-identical objects such as objects of different types), it is possible to determine the type of object which is connected to a certain detected marker. This enables a navigation system to calculate a situation based not only on the position of marker devices and/or their motion states and/or region states and/or the respective temporal series but also on the type of markers and/or objects detected. To this end, the method in accordance with the invention preferably comprises a step of providing identity data (in particular, marker identity data). Such marker identity data can be included in the marker data or can be deduced from the marker data or by means of the marker data. The marker identity data can for example include information about the identity of a marker device and preferably about the type or identity of an object which is connected to said marker device. Since the identity of the marker device (identity data) can be determined from the marker data, it can be a condition and can be included in the condition data. The identity then represents another condition in accordance with which the control flow is controlled. Using such identity data, marker devices can be identified and distinguished from one another, in particular by using a predetermined (known) specific relative spatial relationship (more specifically, a specific geometric arrangement) of the markers in the marker device. This known relationship can be compared with the relationship described by the marker data in order to identify the marker device. To this end, the marker data preferably comprise information on the positions of individual markers of a marker device. Information on such a relationship (the specific geometric arrangement) represents default information. This default information can be provided to the data processing method separately or can be included in the marker data or condition data. The default information can in particular be provided in the form of a look-up table which can be stored in a memory of the surgical navigation system which is used to implement the method in accordance with the invention. An instruction pattern can thus be dependent not only on the positions of marker devices but also on their identity. An instruction pattern can be defined by specifying the identity of at least one marker device (for example by using identity data) in addition to other conditions such as for instance conditions for the region state (such as the presence in or absence from a particular region) and/or motion state of said at least one marker device. As mentioned above, the marker data can then be used to ascertain a geometry of markers, in particular the positions of markers relative to one another (their specific geometric arrangement) when used in the marker device. By comparing the determined geometry of the markers with the identity data in the look-up table, the marker device and preferably also the object connected to it can be identified. Identifying a certain object, for instance an implant or instrument which is for instance commonly used to manipulate a specific anatomical structure in a particular region of the field of view of the detection device, can thus lead to a modification of the control flow, for instance the visualisation view and preferably a zoom of the visualisation view, since the surgical navigation system will for example be able to tell that the user wishes to manually manipulate the displayed anatomical structure. In accordance with one embodiment of the invention, the display device can first be instructed to depict the specific anatomical structure, i.e. to switch to this graphic view. Once the corresponding instruction pattern has been ascertained, the display device is preferably instructed to modify the way in which the anatomical structure is displayed.

Controlling the control flow can also involve controlling an instrument, in particular a measuring instrument such as a microscope, to which a marker device is preferably attached. Detecting an instruction pattern can then lead to the measuring instrument being controlled, for instance by increasing the magnification of a microscope which is used for viewing the site of the operation (which is in particular helpful during neurosurgery on the exposed brain), if another marker device which is for example attached to another instrument moves closer to the marker device which is attached to the microscope. Additionally or alternatively, the instrument to be controlled can be an instrument used for tissue sclerosis, such as a heated wire loop. Once an instruction situation has been detected, the wire loop can be controlled such that an electric current is passed through it in order to begin heating the wire.

Alternatively or additionally, an instruction pattern can lead to a command to the surgical navigation system to modify the operating room lighting, for example to focus a spotlight onto the site of the operation. In general, the method in accordance with the invention can be used to control a control flow of a data processing method which controls any device, in particular a device which is preferably used in computer-assisted surgery.

In accordance with another embodiment of the invention, controlling the control flow can involve triggering a registration procedure in order in particular to register the position of the anatomical part of the body which is of interest in the operation with respect to the reference system of a preoperative image of said part of the body (or vice versa). Upon detecting the respective command situation, the surgical navigation system can then be instructed to assign a certain co-ordinate in the preoperative image to a certain co-ordinate which is being pointed to on the anatomical part of the body with a pointing device, wherein the pointing device can be configured to be detected by the navigation system.

A pointing device such as a pointer can be a rod comprising one or more—advantageously, two or more—markers fastened to it, wherein the pointer can be used to measure off individual co-ordinates, in particular spatial co-ordinates (i.e. three-dimensional co-ordinates), on a part of the body within the framework of a morphing method, wherein a user guides the pointer (in particular, a part of the pointer which has a defined and advantageously fixed position with respect to the at least one marker which is attached to the pointer) to the position corresponding to the co-ordinates, such that the position of the pointer can be determined by using a surgical navigation system to detect the marker on the pointer. The relative position between the markers of the pointer and the part of the pointer used to measure off co-ordinates (in particular, the tip of the pointer) is in particular known. The surgical navigation system then enables the position (of the three-dimensional co-ordinates) to be assigned to a predetermined body structure, wherein the assignment can be made automatically or by user intervention. This assignment is also referred to as a registering and/or registration procedure within the framework of this invention.

The method in accordance with the invention is in particular a data processing method. The data processing method is preferably performed using technical means, in particular a computer. The computer in particular comprises a processor and a memory in order to process the data, in particular electronically. The calculating steps described are in particular performed by a computer. Steps of determining or calculating are in particular steps of determining data within the framework of the technical data processing method, in particular within the framework of a program. A computer is in particular any kind of data processing device. A computer can be a device which is generally thought of as such, for example desktop PCs or notebooks or netbooks, etc., but can also be any programmable apparatus, such as a mobile phone or an embedded processor. In particular, a computer can comprise a system (network) of "sub-computers", wherein each sub-computer represents a computer in its own right. A computer in particular comprises interfaces in order to receive data and/or to perform an analogue-to-digital conversion.

The method according to the invention can be enshrined in a computer program which, when running on a computer or when loaded onto a computer, causes the computer to perform the method as described above, in particular the steps of the method as described above.

Computer program elements of the invention can be embodied in hardware and/or software (including firmware, resident software, micro-code, etc.). The computer program elements of the invention can take the form of a computer program product which can be embodied by a computer-usable or computer-readable storage medium comprising computer-usable or computer-readable program instructions, "code" or a "computer program" embodied in said medium for use by or in connection with the instruction-executing system. Such a system can be a computer; a computer can be a data processing device comprising means for executing the computer program elements and/or the program in accordance with the invention. The computer is in particular used to compare the predetermined pattern with a detected pattern in order to determine and/or identify an instruction pattern. The computer is preferably part of a navigation system. The predetermined variables of the method in accordance with the invention are preferably stored as data, advantageously in the form of a look-up table, in a memory device of a navigation system. Advantageously, the computer also issues the resulting command and/or instruction to an instrument to be controlled, in particular to the display device. Within the context of this application, a computer-usable or computer-readable medium is any medium which can contain, store, communicate, propagate or transfer the program for use by or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s). The computer and/or data processing device can in particular constitute a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated in an instrument).

The computer program and/or parts of it, such as for example individual commands, can also be transmitted between preferably electronic devices by means of a signal wave, in particular a digital signal wave, which carries information representing the program and/or parts of it.

As another aspect of the invention, a navigation system for use in image-guided surgery, in particular computer-assisted surgery (i.e. a surgical navigation system), is disclosed. The navigation system comprises at least a detection device for detecting the positions of the marker devices and a computer configured to perform a method or to execute the program described above.

A further aspect of the invention is a method which comprises the steps, in particular all steps of any of the above described embodiments of a data processing method and further comprises the step of detecting the marker devices by technical means (a marker detection device) in order to generate the marker data used by the data processing method.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for issuing an indication signal (for example, a visual indicating device such as a monitor and/or an audio indicating device such as a loudspeaker and/or a tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data (in particular, predetermined data) which have been stored in said memory beforehand. The computer of the navigation system is preferably used for performing the method and/or executing the program in accordance with the invention.

FIG. 3 shows an instruction pattern being detected using a grid for marker positions.

Figure 1:
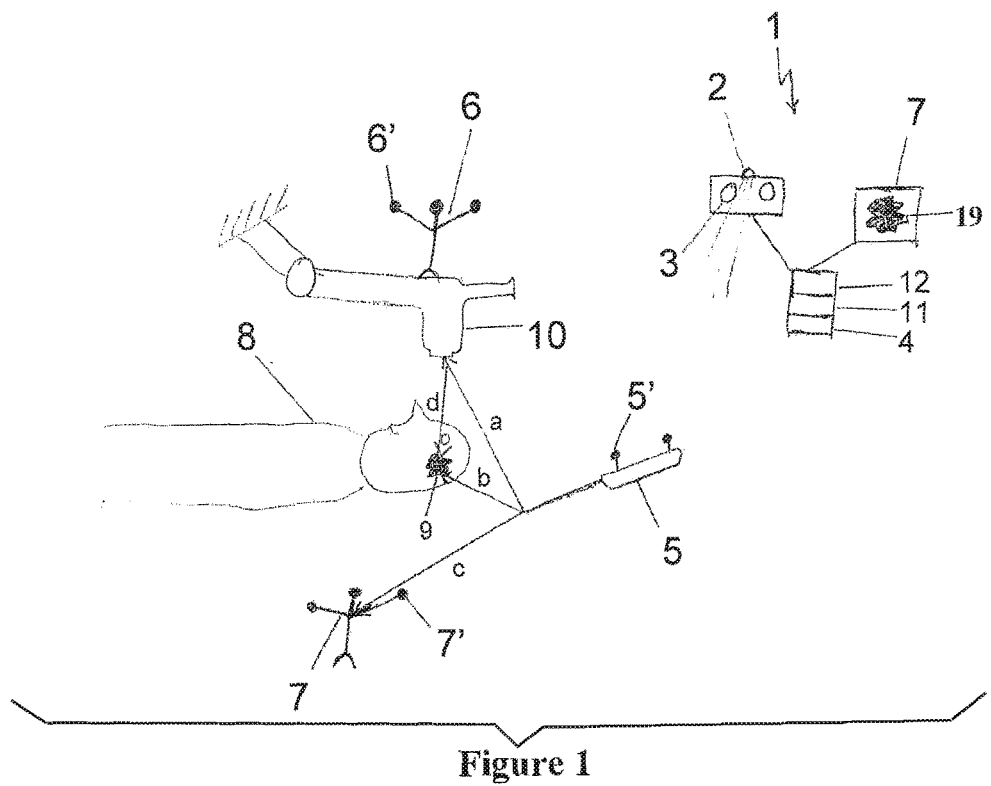
FIG. 1 shows a set-up for determining an instruction pattern using a navigation system.

As shown in FIG. 1, a navigation system 1 comprising an infrared emitter 2 which is used as a transmitter of electromagnetic waves, and a stereotactic camera 3 (as an example of a detection device for detecting infrared radiation reflected from markers 6', 7' which are attached to reference stars 6, 7, and markers 5' which are attached to a pointer 5) is used to detect the markers and therefore the reference stars (marker devices). On the basis of this detection, marker data are generated by the detection device 3 and the navigation system 1. The marker data generated are compared with an instruction pattern by a CPU 4 of the navigation system 1. The navigation system 1 also comprises a computer, in particular a non-permanent memory such as a RAM 12, a processor such as the CPU 4 and a permanent memory such as a hard disc 11. Condition data which comprise the instruction pattern are for instance stored in the permanent memory 11. The navigation system 1 is also provided with a graphic output device such as a monitor 7.

In the set-up depicted in FIG. 1, a microscope 10 (in particular, a microscope which is capable of digital image processing, i.e. a digital microscope) is used to view an anatomical region 9 of a patient 8 which is of interest to a user. The region 9 of interest can for example be a tumour or part of a bone. A pointer 5 with marker elements 5' attached to it is also detected by the navigation system 1; in particular, the position of the pointer 5 relative to the reference stars 6, 7 is determined. Alternatively or additionally, a distance a between a part of an instrument such as the microscope 10 and for example the distal end of the pointer 5 can be determined if there is for example a known and fixed spatial relationship between the reference star 6 and a specific part of the instrument—in the example shown, the lens of the microscope 10. The distance c between the distal end of the pointer 5 and the reference star 7 can be determined by the navigation system 1 in a similar way. If there is a known and fixed relationship between the reference star 7 and the region 9 of interest and/or between the reference star 6 and the region 9 of interest, then it is also possible for the navigation system 1 to determine a distance b between the distal end of the pointer 5 and the region 9 of interest.

The condition data can comprise an instruction pattern which defines a threshold distance for the distance b. If, for example, the distance b as determined on the basis of the marker data remains below the threshold distance (of for example 1 cm or 30 cm or 1 m or a value within a range having a lower limit of 1 cm and/or an upper limit of 75 cm) for a certain length of time or for at least a certain length of time (of for example 1 second or 5 seconds or a value within a range having a lower limit of 1 second and/or an upper limit of 10 seconds), which can be referred to as a threshold time, then the condition defined by the condition data is met. The threshold time preferably denotes a lower limit of a time interval during which a threshold distance is for example maintained; more preferably, the two conditions taken together define the instruction pattern (i.e. a condition for a relative spatial arrangement of the pointer 5 and the reference star 7). Whether the marker data meet the conditions defined by the instruction pattern can for example be identified by the navigation system 1 by comparing the detected situation (i.e. the detected distances and/or times as described by the marker data) with the conditions defined by the instruction pattern. If the comparison leads to a positive result (i.e. the conditions are met), then the control flow is controlled (changed). The positive result is thus transformed (translated) into an instruction and/or command which for example leads to a change in the graphic representation 19 on the monitor 7. After the change, the monitor 7 for example displays an enlarged graphic representation 19 of the anatomical region 9 of interest, wherein the image data are generated by the microscope 10 which is preferably a digital microscope and transmits image data to the surgical navigation system 1.

In order to transform the positive result of the comparison into a control flow statement, a statement database is preferably consulted. The statement database includes allocations (links) between conditions and control flow statements. This database is for instance included on the hard disc 11. The statement database for example describes a link between the condition "distance b smaller than threshold distance" and a control flow statement "enlarge graphic representation". The statement database can also define a link between the condition "distance b smaller than threshold distance" and the control flow statement "demagnify graphic representation" (i.e. zoom out).

Figure 2A:
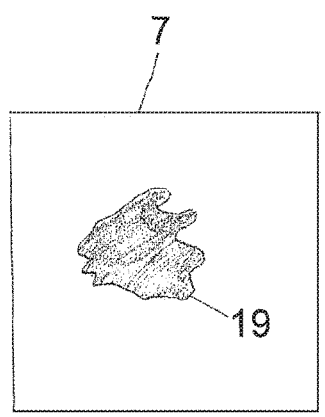
FIG. 2a shows a graphic representation of an anatomical region of interest, before an instruction pattern has been detected.
Figure 2B:
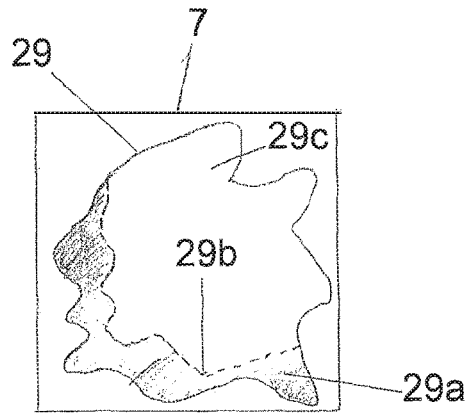
FIG. 2b shows a graphic representation of an anatomical region of interest, after an instruction pattern has been detected.

FIG. 2*a* shows the graphic representation 19 of the region 9 of interest on the monitor 7, before an instruction pattern has been detected. The graphic representation 19 is in particular in a normal mode which is selected by the navigation system 1 as a default representation of the image data detected by the microscope 10. FIG. 2*b* shows a change in the graphic representation 19, such that the graphic representation 29 is obtained. The visual output 29 has in particular been enlarged (zoomed-in on), i.e. magnified, as compared to the graphic representation 19. The colour of certain parts of the graphic representation can also be changed, such that for example only a boundary of the region 9 of interest is depicted in the graphic representation 29.

The instruction pattern can be defined such that a positive result of the comparison is only determined if other distances a, c, d fulfil a certain condition with regard to a threshold distance and/or a threshold time. The result of the comparison is for example only positive if the distance between the microscope 10 and the region 9 of interest is smaller than a threshold distance. In accordance with another example, the instruction pattern can be defined as above with respect to the distance a, but also incorporate the condition that the distance c fulfil an analogous condition. Alternatively or additionally, the distances b and c can be used to define instruction patterns other than the above-mentioned instruction situation, which for example have to be fulfilled at the same time as the instruction situation defined on the basis of the distance a. Thus, an instruction pattern can define a plurality of conditions for the spatial arrangements of marker devices and/or changes in said arrangements. The instruction pattern can also be linked to a plurality of control flow statements, such that if the conditions of an instruction pattern are met, a plurality of control flow statements are executed by the data processing method. In addition to the graphic magnification process described above, additional graphic modifications can for example be made to the graphic representation, in parallel with magnifying the graphic representation, when an instruction pattern defined by the distances b and/or c is detected. The instruction patterns can of course also be defined so as to be independent of one another, i.e. such that they can lead to an instruction irrespective of whether conditions relevant to other (different) instruction patterns are fulfilled.

In particular, a delineation 29*b* between a graphically highlighted part 29*a* and a default representation part 29*c* of the graphic representation 29 can be displayed, when it is detected that distance b has met a certain threshold distance condition and the above-mentioned condition for the distance a is also fulfilled. Thus, further modifications to the graphic representation 29 can be made in the visualisation view on the monitor 7, while the anatomical region 9 of interest continues to be displayed at an increased magnification. Two conditions defined by the instruction pattern are thus fulfilled simultaneously, i.e. at the same time. In accordance with the invention, it is also possible to define an instruction pattern on the basis of the detected length of the distance c (which should preferably be less than a certain threshold distance, preferably for a certain threshold time interval). If it is determined that the marker data also fulfil a condition for the distance c (defined by the same or another instruction pattern), then this can for example result in a patient registration wizard being initialised. If such a patient registration is for example performed during the above-mentioned magnification of the region 9 of interest in the visualisation view, it is possible to increase the level of precision of the registration process.

In accordance with the invention, controlling an auto-zoom function is also an example of a control flow statement which is initiated if the marker data fulfil conditions defined by an instruction pattern. A positive zoom ratio, i.e. a magnification, can for example be initialised if the marker data indicate that an entity, for example an instrument such as the pointer 5, is remaining in a fixed spatial relationship, in particular at a constant distance, to another entity (such as for example the reference stars 6 and/or 7). Preferably, the corresponding condition can be defined by the instruction pattern to the general effect that the pointer 5 is not moving (in particular relative to another entity such as for example a reference star 6, 7). By analogy, the movement of the pointer 5 (as described by the marker data) can then fulfil the conditions of an instruction pattern for zooming the graphic representation out again, in particular for demagnifying the graphic representation 29 and/or reducing the zoom ratio, when the pointer 5 is moved again. This condition can, however, also be defined so as to be dependent on the velocity of the movement of the pointer 5 (in particular by way of a threshold velocity, specifically a velocity of the pointer 5 relative to the reference star 7) which is detected (thus representing a condition for a change in the relative spatial arrangement of the pointer 5 and the reference star 7). A fast movement of the pointer 5 can for example lead to the zoom ratio being reduced, whereas a slow movement of the pointer 5 fulfils an instruction pattern which keeps the zoom ratio constant. A fast movement of the pointer 5 can then for example be defined as a movement at a velocity of more than 3 mm per second or about 3 mm per second, and a slow movement of the pointer 5 can correspondingly be defined as a movement at a velocity of less than 3 mm per second or less than about 3 mm per second. The time required by the navigation system 1 to increase a zoom ratio can for example be defined as three seconds from the initial zoom ratio to the zoom ratio to be achieved (which can be referred to as the target zoom ratio), such that a user is able to stop the zooming action if the target zoom ratio is reached. A corresponding instruction to stop the zooming action can then be created, again for example by a certain and/or predetermined movement of the pointer 5. The time required to change the zoom ratio can for example be about 1 second.

An instruction pattern can preferably be defined such that if the pointer 5 is placed aside, for example onto an instrument table, this can lead to the image detected by the microscope 10 being magnified to a size corresponding to the whole of the available screen surface of the monitor 7. If the pointer 5 is placed aside, this can in particular represent a situation which is normally created when the surgeon wishes to start operating on the region 9 of interest. Thus, an instruction pattern is preferably defined accordingly.

The threshold velocity of the movement of the pointer 5 which distinguishes a fast movement from a slow movement and thus defines the conditions of an instruction pattern can be adapted to the requirements of an individual user. It can in particular be adapted to a tremor which the user's hand exhibits habitually or over an average length of time. This prevents minor movements of the pointer 5 from being misinterpreted as an instruction pattern by the navigation system 1. A certain error and/or tolerance margin can in particular be applied to any threshold condition (such as the aforementioned threshold distance and/or threshold time and/or threshold velocity), in order for example to allow for user-dependent deviations when applying the method in accordance with the invention. In particular, a condition that a translational movement has to be above a minimum movement can represent a threshold condition defined by an instruction pattern.

In accordance with the invention, it is also possible to lock the auto-zoom (this is also referred to as a zoom lock). The lock can in particular be activated if the marker data fulfil a corresponding instruction pattern. Locking the auto-zoom means that the zoom ratio is kept constant, even if subsequent marker data indicate that the conditions of other instruction patterns relating to changing the zoom ratio have been met. Once the auto-zoom is released again (for example by a similar interaction as is used to lock it in the first place), the navigation system will again respond to detected instruction patterns relating to changing the zoom ratio, as before.

The zoom ratio to be reached when using the auto-zoom function can also be limited to a certain factor, such as for example 300% of a default and/or initial zoom ratio which obtains before the corresponding instruction pattern is detected.

Figure 3:
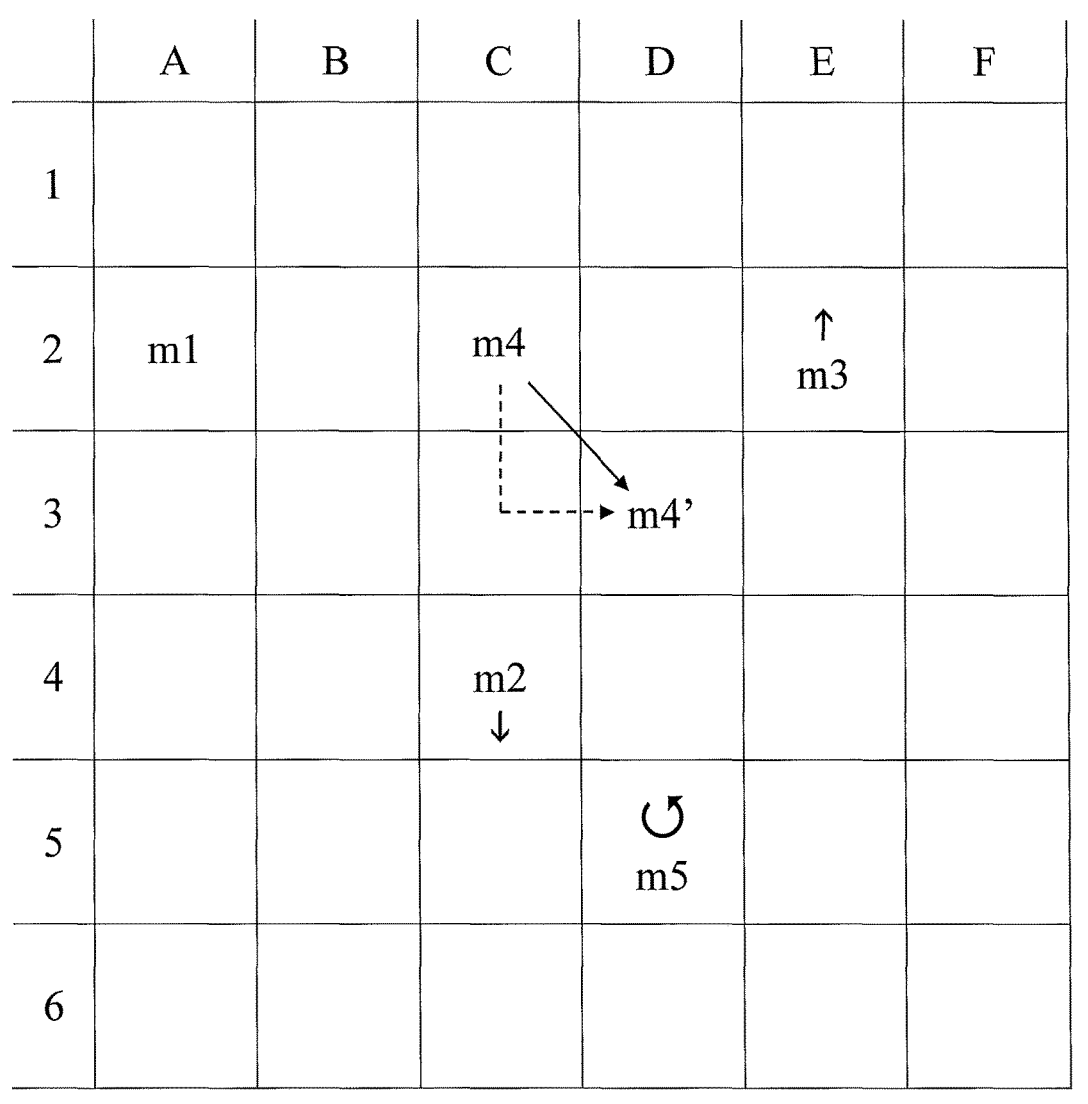

FIG. 3 discloses an embodiment of the invention which relates to defining an instruction pattern using a co-ordinate grid and in particular to defining a region pattern and/or motion-region pattern. A co-ordinate system in which the marker devices can be positioned is in particular divided into preferably polygonal grid zones and/or grid volumes, depending on the dimensionality of the co-ordinate system. Thus, in order to determine whether the marker data meet the conditions of an instruction pattern, the positions of the marker devices (as described by the marker data) are determined in and/or using a grid-based co-ordinate system. An area (for example the operating area) in which the positions of marker devices m1, . . . , m5 can be expected is divided into grid zones A1, . . . , A6; . . . ; F1, . . . , F6. Preferably, the grid zone and/or grid volume in which the positions of the marker devices lie are determined. The grid zones in the example shown are square, but any other (planar) geometries such as triangles or higher-order polygons are also conceivable. The grid shown in FIG. 3 is arranged in a two-dimensional geometry. However, a three-dimensional geometry (i.e. a spatial grid) can also be used in accordance with the invention. In the case of a three-dimensional geometry, the grid zones can therefore also be formed by three-dimensional zones, in particular volumetric zones. The faces of such volumes can be formed by planar geometries such as those used in the two-dimensional grid zones described before. The volumes therefore preferably display a polyhedral geometry. The grid can be regular or irregular, i.e. can exhibit regular (in particular consistent) or irregular (in particular inconsistent) spacing between nodes. Boundaries between grid zones and/or grid volumes can be assigned as part of one contiguous grid zone and/or grid volume or at least two contiguous grid zones and/or grid volumes. If the marker data describe a position of a marker device on an intersection of boundaries, in particular at the corner (specifically, a corner boundary) of a grid zone and/or grid volume, the position can be determined to be lying in any one of the contiguous grid zones and/or grid volumes or in one or more specific contiguous grid zones and/or grid volumes of the contiguous grid zones and/or grid volumes.

The grid can be used to determine a pattern of positions of the marker devices m1, . . . , m5. Such a pattern can for example be formed by a detected movement of the marker m2 in a direction from grid zone C4 to grid zone C5, i.e. across an in particular shared boundary between preferably two grid zones. This movement of the marker device m2 can be determined by first measuring its position in grid zone C4 and subsequently measuring the position of the marker device m2 in grid zone C5. An instruction pattern can be defined such that only the determined pattern of one marker device, for example the marker device m2, causes a control statement to be executed. Alternatively or additionally, another position pattern of a different marker device can be required in order to meet the conditions defined by an instruction pattern. For example, a movement of the marker device m3 across the boundary between grid zones E2 and E1 at the same time as the movement of the marker device m2 can represent a condition of the instruction pattern. However, the movement of the two marker devices m2, m3 can also occur at different points in time (i.e. temporally offset); in particular, the movements of the two marker devices m2, m3 can be offset in time such that the movement of one marker device has in particular been completed before the movement of the other marker device commences. The instruction pattern described can be further enhanced and/or limited by additional conditions for a synchronous or temporally offset position pattern of other marker devices, for example by setting a condition for the marker device m1 to be at rest, in particular for the marker device m1 to be at rest in a defined grid zone such as for example zone A2 (i.e. for the marker device m1 to maintain its position within and/or at the boundaries of grid zone A2).

Additional or alternative conditions in accordance with this embodiment for determining an instruction pattern can for example relate to a distance between two marker devices. The number of grid zones lying between the grid zones occupied by for example two specific marker devices can for example be used to determine a condition of an instruction pattern. In the example shown, the two grid zones B3 and C4 lying diagonally between the positions of the marker devices m1 and m5 in grid zones A2 and D5, respectively, can be used to determine the distance between the marker devices m1 and m5.

As another example of an alternative or additional condition, a trajectory of the marker device m5, in particular a translational movement along a predefined path, can be used to define an instruction pattern or part of an instruction pattern.

Conditions of an instruction pattern can also be defined by a marker device being located in specific grid zones or performing a movement between specific (i.e. preferably predetermined) grid zones and in particular starting its movement in a defined grid zone and finishing its movement in another defined grid zone. Such a pattern is shown for the movement of the marker device m4 from grid zone C2 to grid zone D3. This pattern can be path-dependent, i.e. in particular if the condition specifies a path through other grid zones which the marker device m4 passes through between leaving its position in grid zone C2 (indicated in FIG. 3 as the marker device m4) and arriving at the position in grid zone D3 (indicated in FIG. 3 as the marker device m4'). For example, it is possible for this movement to pass through grid zone C3, as shown by the dashed arrow in FIG. 3. However, it is also possible to use only the start and finish grid zones, in particular if the marker device m4 moves diagonally between grid zones C2 and D3, crossing the shared corner boundary, as indicated by the solid arrow in FIG. 3.

The geometry of the grid used is preferably stored in a look-up table which is used by the navigation system. This grid is then preferably referenced (i.e. in a fixed and known geometric relationship) to the reference system used for determining the positions of the marker device or devices. This embodiment thus has the advantage that even a pattern derived from the positions of only one marker device can be used to define an instruction pattern. However, it is preferable to use the position patterns of at least two marker devices to define an instruction pattern. This has the advantage that the instruction will be situation-dependent and reliably detectable and that a multitude of instruction patterns can be defined in a similar way to the multitude of commands which are commonly given to a navigation system in order to perform the method of the invention. In particular, this also allows a condition for a relative spatial arrangement and/or a change of the relative spatial arrangement of the marker devices m1, . . . , m5 to be applied. This spatial arrangement and/or changes to it in particular reflect the situation in an operating theatre.

Preferably, the condition data include not only the spatial arrangement of the marker devices and/or changes to it but also identity data, such that the number of possible instruction patterns is increased. The marker devices m1, . . . , m5 can for example each be of a different type. The positions of the markers which are respectively attached to each of the marker devices m1, . . . , m5 are in particular unique to the marker device in question and can thus be distinguished from one another. These distinguishable marker devices m1, . . . , m5 are preferably attached to objects such as medical instruments and/or parts of the body, in order to be able to distinguish between these objects and to ascertain the type of object which is present in and/or absent from a grid zone and/or grid volume. One of the distinguishable marker devices m1, . . . , m5 can for example be attached to a pointer 5. Thus, the conditions for a detected pattern to be an instruction pattern can be based not only on the positions of the marker devices m1, . . . , m5 but also on the type of marker devices m1, . . . , m5 occupying the detected position.

This embodiment also has the advantage that it is possible to determine the number and/or type of the marker devices m1, . . . , m5 which are present in a particular grid zone and/or grid volume (or a predetermined area and/or volume comprising a plurality of in particular at least two grid zones and/or grid volumes). It is thus also possible to determine the presence and/or absence of certain objects in such a grid zone and/or grid volume or predetermined area and/or volume, using marker identity data. A corresponding indication signal (for example, a visual and/or acoustic signal) can also be outputted to the user in order to notify the user of such a determination result. This signal can be outputted by the indication device of the navigation system.

The commands to be issued by the surgical navigation system when an instruction pattern has been determined can relate to a change in the graphic representation, as described above. However, commands relating to commencing a drilling process or operating a light switch in order to illuminate for example the site of operation are also possible within the scope of the invention.

Figure 4:
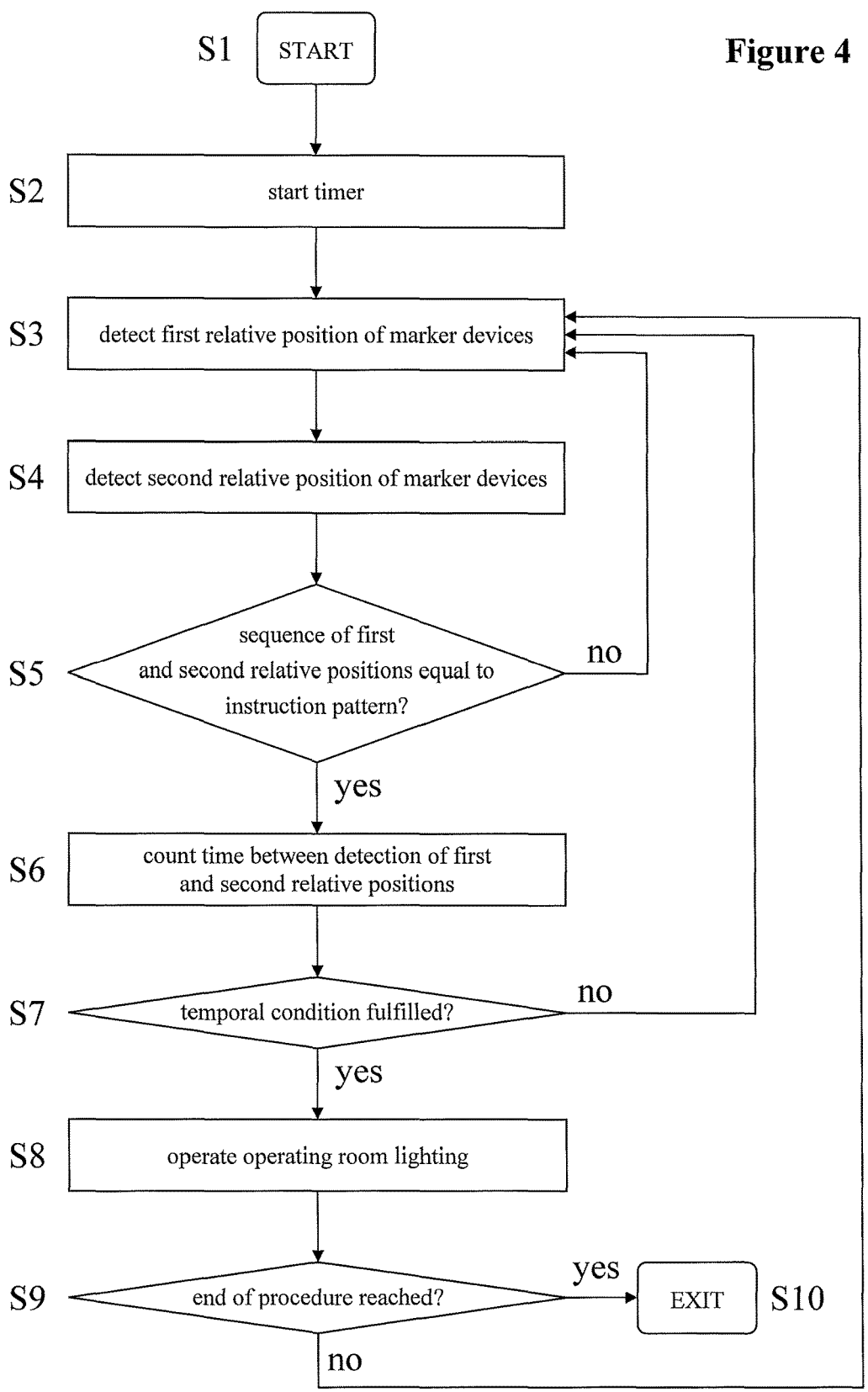
FIG. 4 shows a flow diagram of one embodiment of the method in accordance with the invention.
Figure 5:
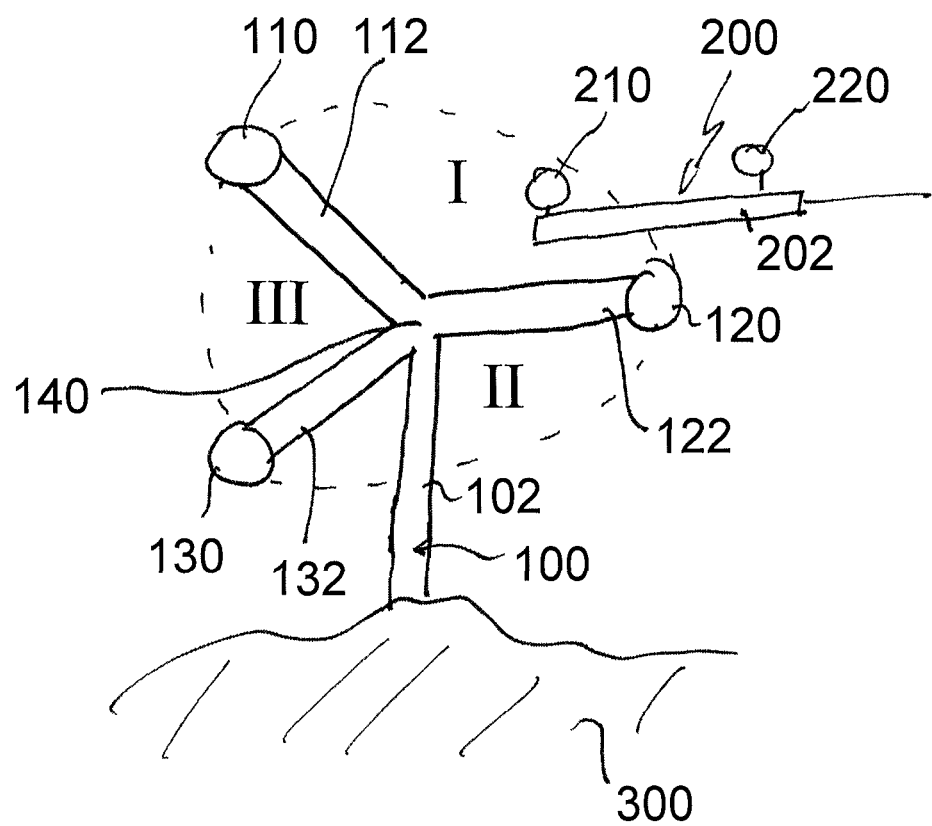
FIG. 5 shows the operating space being partitioned into regions using a marker device.

FIG. 4 shows a flow diagram which illustrates an embodiment of the data processing method in accordance with the invention. In step S1, the data processing method is initiated, for example by triggering a corresponding procedure and/or program on the computer of the navigation system 1. In step S2, a timer (for example, an internal clock of the computer) is started in order to count the length of time which passes while the data processing method is performed. In step S3, the method continues by detecting a first relative position of at least two marker devices (for example, the marker devices 5, 6, 7 from the embodiment of FIG. 1 or the marker devices m1, . . . , m5 from the embodiment of FIG. 3) and thus generating corresponding marker data. The marker data can be detected using a navigation system 1 as described for the embodiments of FIGS. 1 and 3. Subsequently, in step S4, a second relative position of the at least two marker devices is detected, and corresponding marker data are generated (for example by the computer 4). In step S5, the sequence of first and second relative positions is evaluated on the basis of the marker data generated (preferably in the order in which the relative positions were detected) as to whether it corresponds and/or is equal to a predefined instruction pattern defined by the condition data. To this end, a number of instruction patterns are preferably predetermined and stored in a look-up table on the hard disc 11 of the navigation system 1, in order to be read off and compared with the sequence of detected relative positions. If it is determined in step S5 that the sequence of relative positions is not equal to an instruction pattern (i.e. the result in step S5 is "no"), the method returns to step S3 and again starts to detect relative positions. If it is determined in step S5 that the sequence of relative positions is equal to an instruction pattern (i.e. the result in step S5 is "yes"), the time which passed between detecting the first relative position and detecting the second relative position is counted on the basis of the marker data; in particular, the length of time which passed between the two detections (the time interval between steps S3 and S4) is counted. Step S7 then continues the method by evaluating whether the time counted in step S6 fulfils a predetermined condition which can be part of a time-dependent pattern of relative positions and which is defined by the condition data. If the time counted in step S6 is combined with information on a distance between the relative positions ascertained in steps S3 and S4 (which is in particular possible if a third reference position is determined), a pattern of motion states can be ascertained in step S7, resulting in a comparison of velocity values, which are preferably determined (i.e. calculated) on the basis of the marker data, with predetermined velocity values which are included in the condition data and advantageously stored in a look-up table on the hard disc 11 of the navigation system 1. The predetermined temporal condition used in step S7 can however also be a predetermined time interval which the time counted in step S6 should not exceed. If the temporal condition is not fulfilled, the method in accordance with the invention returns to step S3 and again starts to detect first relative positions. If the temporal condition is fulfilled, the method proceeds to step S8. Step S8 relates to controlling a control flow by executing a control flow statement. In the example of FIG. 5, step S8 comprises the action of controlling the operating room (OR) lighting, in particular operating the lighting such as switching it on or off or dimming it. In the subsequent method step S9, an evaluation is made as to whether the end of the procedure (i.e. the method in accordance with the invention) has been reached, for example by a user entering a manual command to exit the method. If the end of the procedure has been reached, the method in accordance with the invention is exited in step S10. If it is determined in step S9 that the end of the procedure has not been reached, the method in accordance with the invention returns to step S3 and again starts to detect first relative positions.

The time which elapses while the method in accordance with the invention is performed is measured by starting the timer in method step S2. This can be used as an absolute time measure—for example, points in time and/or time intervals can be determined in step S6 by considering individual time stamps associated with performing steps S3 and S4, in particular in order to calculate a time interval (which can preferably be calculated by subtracting the value of the time stamp for step S4 from the value of the time stamp for step S3).

FIG. 5 shows a reference array 100 which represents an example of a marker device. The reference array 100 comprises three marker spheres 110, 120 and 130 at the end of three arms 112, 122 and 132, respectively. The arms 112, 122 and 132 are fixed to a shaft 102 of the reference array 100. The arms 112, 122 and 132 divide the space around the reference array 100 into regions I, II and III. The regions can be defined with respect to the position of the marker device 100. In the embodiment shown in FIG. 5, the regions can in particular be defined with respect to the centre position 140 at which the three arms 112, 122 and 132 are fixed together. The regions I, II, III can be defined within a sphere around the centre position 140. This sphere can exhibit a radius which corresponds to the length of one of the arms 112, 122 and 132. Moreover, the region I can be defined to include points which are closer to the arms 112 and 122 than to the arm 132. Correspondingly, the region II can be defined to include points which are closer to the arms 122 and 132 than to the arm 112. Finally, the region III can be defined to include points which are closer to the arms 112 and 132 than to the arm 122. In this way, the three regions I, II and III are defined, on the basis of the position of the arms 112, 122 and 132, within the aforementioned sphere which is defined by the centre position 140.

In accordance with another embodiment, the part of the surface of the arm 112 which is close to the region I is given a particular colour, for instance yellow. The same colour is given to the part of the surface of the arm 122 which is close to the same region, i.e. region I. Another colour, for instance green, is given to the part of the surface of the arm 122 which is close to the region II. The same colour is preferably given to the part of the surface of the arm 132 which is close to the region II. Yet another colour, for instance red, is given to the part of the surface of the arm 132 which is close to the region III. The same colour is preferably given to the surface of the part of the arm 112 which is close to the region III. In this way, it is obvious to a user that a particular colour has been given to each of the regions I (yellow), II (green) and III (red), respectively.

An instrument 200 is preferably provided which comprises a rod-shaped part 202 to which marker spheres 210 and 220 are attached. In accordance with this particular embodiment, the marker sphere 210 is a marker which represents a marker device in its own right.

In accordance with one embodiment, the condition for the spatial arrangement of a marker device is that the marker device is within one of the regions I, II or III. The marker device can for example consist of only one marker sphere 210 or can for example include both the marker spheres 210 and 220. In accordance with another alternative embodiment, the marker device can also be the instrument 200, and the condition can be that the instrument 200 is within one of the regions I, II, and III. The presence or absence of a marker device in a region can be defined to the effect that it is completely or only partly in said region. In the example shown in FIG. 5, the marker device 200 is only partly in the region I, while the marker device 210 is completely within the region I.

In the example shown in FIG. 5, the marker data describe a situation in which the aforementioned condition is fulfilled, i.e. the marker device 210 is within the region I. Thus, the control flow will be controlled in accordance with a control flow statement which is dependent on this condition having been met.

It is of course advantageous for the user to know the type of control flow statement which is dependent on one of the conditions being met. In other words, it is advantageous for the user to know the type of control flow statement which is executed if for example the user enters one of the regions I, II or III with the marker device 210. To this end, a display is preferably provided (for instance, the monitor 7 of FIG. 1). This display, which is in particular a GUI, displays a "next" button, preferably in green or with a green outline, a "back" button in red and a "screenshot" button in yellow. The user then knows that moving the instrument 200 between the yellow-marked part of the arms 112 and 122 will result in a screenshot. The screenshot represents a control flow statement for storing the current image content of the screen which in particular shows the location of the instrument 200 relative to a patient or part 300 of the patient's body such as for example the bone structure 300 in FIG. 5. In this way, it is possible to document the surgical operation without touching a screen or keyboard.

As mentioned above, either one marker sphere alone or several marker spheres, attached for example to a handle, can be used in order to select a control flow statement. In the above example, the instrument 200 was used. This has the advantage that no additional tool is required in order for the surgeon to select the control flow statement. In particular, there is no need to calibrate an additional instrument or tool.

Additional examples of control flow statements, in particular for a sequence of control flow statements which can be initiated using the present invention, are discussed below.

A control flow statement can for example correspond to selecting another control flow statement (in particular an instruction, such as in particular an action) which is to be performed when another control flow statement, which corresponds to triggering the instruction, in particular an action, is subsequently initiated. An example of an action would then for example be the aforementioned screenshot or a zooming-in or zooming-out action.

Figure 6:
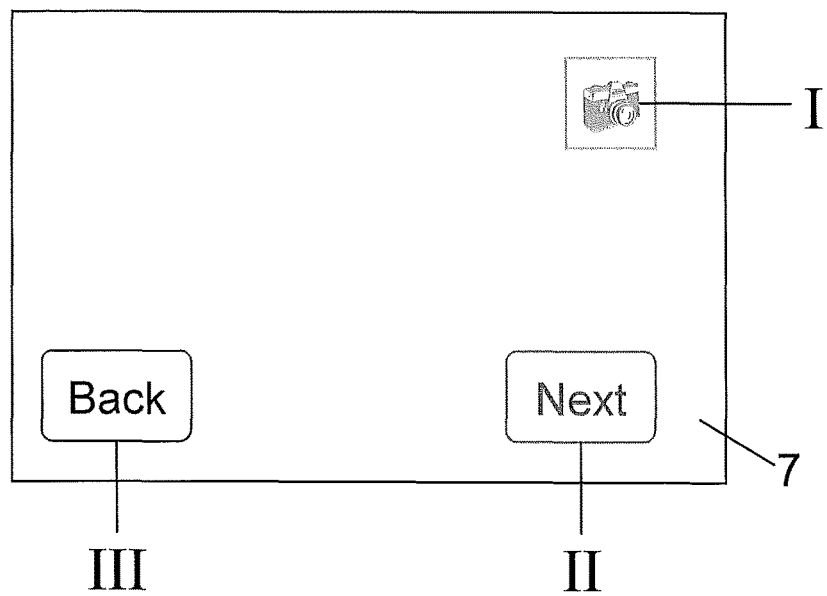
FIG. 6 shows a display which provides information about control flow statements associated with the regions of FIG. 5.
Figure 7:
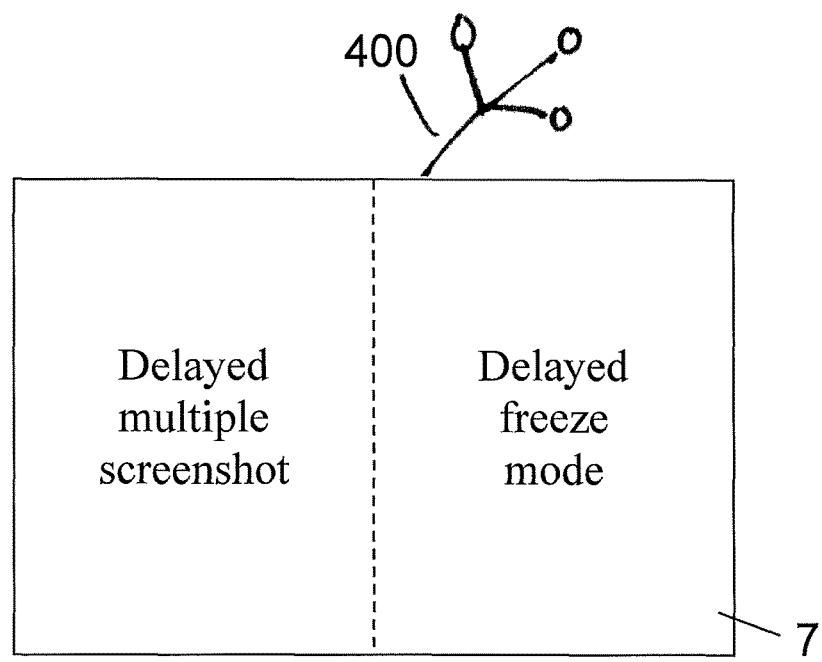
FIG. 7 shows a display for initiating control flow statements using an instrument.

FIG. 7 shows another example of a display 7. A marker device, for instance the reference star 400, is attached to the display 7. The relative position between the reference star 400 and the display 7 is stored in the computer of the navigation system. Thus, if a user approaches the display 7 with the instrument 200, the navigation system can for example calculate whether the instrument 200 is close to the left-hand side or the right-hand side of the display 7. A condition is then preferably defined on the basis of a distance between the instrument 200 and the left-hand side or the right-hand side of the display 7. If the instrument 200 is within said distance, this initiates a control flow statement. In the example shown in FIG. 6, approaching the left half of the display 7 causes another control flow statement, entitled "delayed multiple screenshot", to be selected. It is of course equally possible, in accordance with an alternative embodiment, to use a keyboard or to press a button on a display in order to select this control flow statement. The user can then move the instrument to several points of interest and keep the instrument still for a certain length of time, since the condition data preferably specify that a marker device, in particular the specified marker device 200, has to be within a region (for example, close to the point of interest such as for example a patient's bone) for a predetermined length of time in order to trigger the selected control flow statement. Thus, if the user for example holds the instrument 200 close to the bone structure (to which a marker device is also attached) for the predetermined length of time, then said other control flow statement is triggered. Since the control flow statement "delayed multiple screenshot" had been selected beforehand, holding the instrument close to the bone triggers the screenshot. Thus, a sequence of control flow statements (such as for example selecting and triggering) can be initiated using the marker devices in accordance with the invention. In accordance with another embodiment, a control flow statement is executed—for example, a screenshot is taken—if the marker device 200 is kept still within a predefined region which in particular includes the patient. The screenshot in particular shows the location of the marker device relative to the patient and is in particular matched with analysis data of the patient such as CTs or MRTs, as is usual in computer-assisted surgery.

Once the screenshots have been taken, the surgeon can deactivate the "delayed multiple screenshot" button, for instance by again approaching the left-hand side of the display 7 with the instrument 200. Alternatively, a "delayed single screenshot" button can be activated in order to take a single screenshot only, wherein this button is automatically deactivated again once the single screenshot has been taken.

In accordance with another embodiment, a condition (an instruction pattern) specifies that the user keeps the instrument still within a region (for example, at a point of interest) for a certain length of time. The marker data indicate that the instrument has been kept still for a certain length of time. If the marker data are compared to the condition data, then the condition of being at rest in a particular region for a predetermined length of time is met if the length of time indicated by the marker data is equal to or longer than the predetermined length of time. A control flow statement is then initiated, which for instance causes the current tracking positions and any other important information to be stored. The aforementioned region can in particular be identical to the region which can be observed by the navigation system or can be restricted to regions which are close to and/or include particular parts of the patient's body. Once initiated, the control flow statement thus preferably causes the position and in particular the path of the instrument to be stored. The user can then preferably be guided by initiating the "delayed freeze mode" by approaching the right-hand side of the display 7 with the instrument 200. Specifically, the control flow statement referred to as "delayed freeze mode" causes the user to be provided with signal-guidance information for moving the instrument to the same location at which the user held the instrument 200 for said certain length of time beforehand. In brain surgery in particular, this can be advantageous when following at least parts of exactly the same path as is being signalled to the user, for example via the display.

Features of different embodiments of the invention as described above can be combined with one another, providing such combinations are technically expedient and feasible.

The invention claimed is:

1. A method of directing a control flow of an associated navigation system in computer-assisted surgery responsive to direct manual manipulation of a single marker device, the method comprising:
    providing marker data which describe a temporal series of detected positions of the single marker device as a temporal and spatial movement pattern of the detected positions of the single marker device, wherein the movement pattern is generated by the direct manual manipulation of the single marker device, wherein the detected positions of the single marker device are defined in an associated grid divided into a plurality of delineated predetermined geometric divisions in which the single marker device can lie;
    providing condition data comprising an instruction pattern defining one or more predetermined conditions of the temporal and spatial movement pattern of the detected positions of the single marker device, wherein the one or more predetermined conditions of the temporal and spatial movement pattern comprises a condition defining a predetermined sequence of the delineated predetermined geometric divisions through which the single marker device is to pass in order to create the instruction pattern;
    determining, based on the marker data and the condition data, whether the temporal and spatial movement pattern of the detected positions of the single marker device fulfill the one or more predetermined conditions; and
    in accordance with determining the fulfillment of the one or more predetermined conditions, selectively generating a first control flow instruction for use by the associated navigation system to control the control flow of the associated navigation system, wherein the associated navigation system is responsive to receiving the selectively generated first control flow instruction to modify an order in which steps of the control flow are executed by a computer of the associated navigation system to initiate following a first sequence of steps of the control flow, or in accordance with determining the non-fulfillment of the one or more predetermined conditions, selectively generating a second control flow instruction for use by the associated navigation system to control the control flow of the associated navigation system, wherein the associated navigation system is responsive to receiving the selectively generated second control flow instruction to modify the order in which the steps of the control flow are executed by the computer of the associated navigation system to initiate following a second sequence of steps of the control flow, the second sequence of steps of the control flow being different than the first sequence of steps of the control flow.

2. The method according to claim 1, wherein the one or more predetermined conditions of the temporal and spatial movement pattern comprises a condition requiring that the single marker device performs a translational movement.

3. The method according to claim 1, wherein the one or more predetermined conditions of the temporal and spatial movement pattern comprises a motion state condition for the single marker device, said motion state condition comprising one or more of:
 a predetermined velocity of the single marker device;
 a predetermined acceleration of the single marker device;
 a predetermined direction of velocity of the single marker device; and
 the single marker device remaining in a static status for a predetermined length of time.

4. The method according to claim 1, wherein the condition data comprise a time-dependent condition.

5. The method according to claim 1, wherein the condition data comprise a condition derived from a distance between the single marker device and an associated second single marker device.

6. The method according to claim 1, wherein the condition data comprise a condition for an identity of the single marker device.

7. The method according to claim 1, wherein:
 the generating the first or second control flow instruction in accordance with a control flow history.

8. The method according to claim 1, wherein the condition data describe a pattern which represents a predetermined condition for a set of marker devices, the predetermined condition being at least one of:
 a condition for a motion state of a marker device of the set of marker devices;
 a condition for a distance between marker devices of the set of marker devices;
 a condition for a position of a marker device of the set of marker devices; and
 a condition for a presence or an absence of a marker device of the set of marker devices in a region.

9. The method according to claim 1, wherein controlling the control flow comprises determining a control flow statement depending on whether the marker data meet the one or more predetermined conditions defined by the condition data and in accordance with respective assignments between a plurality of different conditions and a plurality of different control flow statements.

10. A method for use in computer-assisted surgery comprising the data processing method of claim 1, wherein providing the marker data comprises:
 detecting one or more of a spatial arrangement of the single marker device and a change in a relative spatial arrangement of at least two marker devices by a marker detection device; and
 generating the marker data based on a result of the detecting.

11. The method according to claim 1, wherein:
 the selectively generating the second control flow instruction in accordance with the determining the non-fulfillment of the one or more predetermined conditions comprises:
 selectively generating a query control flow instruction, wherein the associated navigation system is responsive to receiving the selectively generated query control flow instruction to modify the order in which the steps of the control flow are executed by the computer of the associated navigation system to initiate following the second sequence of steps of the control flow to generate a signal presenting a query to a user of the single marker device; and
 the selectively generating the first control flow instruction in accordance with the determining the fulfillment of the one or more predetermined conditions comprises:
 selectively generating a query response control flow instruction, wherein the associated navigation system is responsive to receiving the selectively generated query response control flow instruction to modify the order in which the steps of the control flow are executed by the computer of the associated navigation system to initiate following the first sequence of steps of the control flow to generate a signal representing a response by the user of the single marker device to the signal presenting the query.

12. The method according to claim 11, wherein:
 the selectively generating the query control flow instruction comprises generating a first control flow statement causing the associated navigation system to present to the user of the single marker device a number of options for continuing a workflow; and
 the selectively generating the query response control flow instruction comprises generating a second control flow statement causing the associated navigation system to execute an option selected by the user of the single marker device.

13. The method according to claim 11, wherein:
 the selectively generating the query control flow instruction comprises generating a first control flow statement causing the associated navigation system to present to the user of the single marker device a query for approval by the user of an instruction proposed by the computer of the associated navigation system; and
 the selectively generating the query response control flow instruction comprises generating a second control flow statement causing the associated navigation system to selectively execute the proposed instruction responsive to the approval by the user of the single marker device.

14. A navigation system for computer-assisted surgery, comprising:
 a computer comprising a processor and a non-transitory computer readable storage medium;
 a single marker device;
 a detection device for detecting the position of the single marker device; and a program stored in the non-transitory computer readable storage medium, the program being executable by the computer to perform a method directing a control flow of the navigation system responsive to direct manual manipulation of the single marker device, the method comprising:

providing marker data which describe a temporal series of positions of the single marker device detected by the detection device as a temporal and spatial movement pattern of the detected positions of the single marker device, wherein the movement pattern is generated by the manipulation of the single marker device, wherein the detected positions of the single marker device are defined in an associated grid divided into a plurality of delineated predetermined geometric divisions in which the single marker device can lie;

providing condition data comprising an instruction pattern defining one or more predetermined conditions of the temporal and spatial movement pattern of the detected positions of the single marker device, wherein the one or more predetermined conditions of the temporal and spatial movement pattern comprises a condition defining a predetermined sequence of the delineated predetermined geometric divisions through which the single marker device is to pass in order to create the instruction pattern;

determining, based on the marker data and the condition data, whether the temporal and spatial movement pattern of the detected positions of the single marker device fulfill the one or more predetermined conditions; and in accordance with determining the fulfillment of the one or more predetermined conditions, selectively generating a first control flow instruction to control the control flow of the navigation system, wherein the navigation system is responsive to the selectively generated first control flow instruction to modify an order in which steps of the control flow are executed by the computer of the navigation system to initiate following a first sequence of steps of the control flow, or in accordance with determining the non-fulfillment of the one or more predetermined conditions, selectively generating a second control flow instruction to control the control flow of the navigation system, wherein the navigation system is responsive to receiving the selectively generated second control flow instruction to modify the order in which the steps of the control flow are executed by the computer of the navigation system to initiate following a second sequence of steps of the control flow, the second sequence of steps of the control flow being different than the first sequence of steps of the control flow.

15. A non-transitory computer-readable storage medium storing a program which, when running on a computer or when loaded onto a computer, causes the computer to perform a data processing method for use in computer-assisted surgery, for directing a control flow of an associated navigation system responsive to direct manual manipulation of a single marker device, comprising:

providing marker data which describe a temporal series of detected positions of the single marker device as a temporal and spatial movement pattern of the detected positions of the single marker device, wherein the movement pattern is generated by the direct manual manipulation of the single marker device, wherein the detected positions of the single marker device are defined in an associated grid divided into a plurality of delineated predetermined geometric divisions in which the single marker device can lie;

providing condition data comprising an instruction pattern defining one or more predetermined conditions of the temporal and spatial movement pattern of the detected positions of the single marker device, wherein the one or more predetermined conditions of the temporal and spatial movement pattern comprises a condition defining a predetermined sequence of the delineated predetermined geometric divisions through which the single marker device is to pass in order to create the instruction pattern;

determining, based on the marker data and the condition data, whether the temporal and spatial movement pattern of the detected positions of the single marker device fulfill the one or more predetermined conditions; and in accordance with determining the fulfillment of the one or more predetermined conditions, selectively generating a first control flow instruction for use by the associated navigation system to control the control flow of the associated navigation system, wherein the associated navigation system is responsive to receiving the selectively generated first control flow instruction to modify an order in which steps of the control flow are executed by a computer of the associated navigation system to initiate following a first sequence of steps of the control flow, or in accordance with determining the non-fulfillment of the one or more predetermined conditions, selectively generating a second control flow instruction for use by the associated navigation system to control the control flow of the associated navigation system, wherein the associated navigation system is responsive to receiving the selectively generated second control flow instruction to modify the order in which the steps of the control flow are executed by the computer of the associated navigation system to initiate following a second sequence of steps of the control flow, the second sequence of steps of the control flow being different than the first sequence of steps of the control flow.

16. A computer comprising:

a processor; and a non-transitory computer-readable storage medium storing a program, the program being executable by the processor to perform a method directing a control flow of an associated navigation system responsive to direct manual manipulation of a single marker device, the method executable by the processor comprising:

providing marker data which describe a temporal series of detected positions of the single marker device as a temporal and spatial movement pattern of the detected positions of the single marker device, wherein the movement pattern is generated by the manipulation of the single marker device, wherein the detected positions of the single marker device are defined in an associated grid divided into a plurality of delineated predetermined geometric divisions in which the single marker device can lie;

providing condition data comprising an instruction pattern defining one or more predetermined conditions of the temporal and spatial movement pattern of the detected positions of the single marker device, wherein the one or more predetermined conditions of the temporal and spatial movement pattern comprises a condition defining a predetermined sequence of the delineated predetermined geometric divisions through which the single marker device is to pass in order to create the instruction pattern;

determining, based on the marker data and the condition data, whether the temporal and spatial movement pattern of the detected positions of the single marker device fulfill the one or more predetermined conditions; and in accordance with determining the fulfillment of the one or more predetermined conditions, selectively generating a first control flow instruction for use by the associated navigation system to control the control flow of the associated navigation system, wherein the associated navigation system is responsive to receiving the selectively generated first control flow instruction to modify an order in which steps of the control flow are executed by a computer of the associated navigation system to initiate following a first sequence of steps of the control flow, or in accordance with determining the non-fulfillment of the one or more predetermined conditions, selectively generating a second control flow instruction for use by the associated navigation system to control the control flow of the associated navigation system, wherein the associated navigation system is responsive to receiving the selectively generated second control flow instruction to modify the order in which the steps of the control flow are executed by the computer of the associated navigation system to initiate following a second sequence of steps of the control flow, the second sequence of steps of the control flow being different than the first sequence of steps of the control flow.

17. A method of directing a control flow of an associated navigation system in computer-assisted surgery responsive to manipulation of a single marker device, the method comprising:

providing marker data which describes detected positions of the single marker device as a spatial and/or temporal movement pattern of positions of the single marker device, the detected positions of the single marker device being defined relative to an associated grid divided into a plurality of delineated predetermined geometric divisions in which the single marker device can lie;

providing condition data which describe a predetermined condition for the spatial and/or temporal movement pattern of positions of the single marker device relative to the plurality of delineated predetermined geometric divisions of the associated grid, wherein the predetermined condition for the spatial and/or temporal movement pattern of positions of the single marker device comprises a condition defining a predetermined sequence of the delineated predetermined geometric divisions through which the single marker device is to pass in order to create the predetermined condition;

determining, based on the marker data and the condition data, whether the spatial and/or temporal movement pattern of the detected positions of the single marker device fulfill the predetermined condition; and responsive to determining the fulfillment of the predetermined condition, selectively generating a first control flow instruction for use by the associated navigation system to control the control flow of the associated navigation system, wherein the associated navigation system is responsive to receiving the selectively generated first control flow instruction to modify an order in which steps of the control flow are executed by a computer of the associated navigation system to initiate following a first sequence of steps of the control flow; or responsive to determining the non-fulfillment of the predetermined condition, selectively generating a second control flow instruction for use by the associated navigation system to control the control flow of the associated navigation system, wherein the associated navigation system is responsive to receiving the selectively generated second control flow instruction to modify the order in which the steps of the control flow are executed by the computer of the associated navigation system to initiate following a second sequence of steps of the control flow, the second sequence of steps of the control flow being different than the first sequence of steps of the control flow.

18. A navigation system for computer-assisted surgery, comprising:

a computer comprising a processor and a non-transitory computer readable storage medium;

a single marker device;

a detection device for detecting the position of the single marker device; and a program stored in the non-transitory computer readable storage medium, the program being executable by the computer to perform a method directing a control flow of the navigation system responsive to direct manual manipulation of the marker device, the method comprising:

providing marker data which describes detected positions of the single marker device as a spatial and/or temporal movement pattern of positions of the single marker device, the detected positions of the single marker device being defined relative to an associated grid divided into a plurality of delineated predetermined geometric divisions in which the single marker device can lie;

providing condition data which describe a predetermined condition for the spatial and/or temporal movement pattern of positions of the single marker device relative to the plurality of delineated predetermined geometric divisions of the associated grid, wherein the predetermined condition for the spatial and/or temporal movement pattern of positions of the single marker device comprises a condition defining a predetermined sequence of the delineated predetermined geometric divisions through which the single marker device is to pass in order to create the predetermined condition;

determining, based on the marker data and the condition data, whether the spatial and/or temporal movement pattern of the detected positions of the single marker device fulfill the predetermined condition; and responsive to determining the fulfillment of the predetermined condition, selectively generating a first control flow instruction for use by the associated navigation system to control the control flow of the associated navigation system, wherein the associated navigation system is responsive to receiving the selectively generated first control flow instruction to modify an order in which steps of the control flow are executed by a computer of the associated navigation system to initiate following a first sequence of steps of the control flow; or responsive to determining the non-fulfillment of the predetermined condition, selectively generating a second control flow instruction for use by the associated navigation system to control the control flow of the associated navigation system, wherein the associated navigation system is responsive to receiving the selectively generated second control flow instruction to modify the order in which the steps of the control flow are executed by the computer of the associated navigation system to initiate following a second sequence of steps of the control flow, the second sequence of steps of the control flow being different than the first sequence of steps of the control flow.

\* \* \* \* \*